(12) United States Patent
Robb et al.

(10) Patent No.: US 12,607,635 B2
(45) Date of Patent: Apr. 21, 2026

(54) METHOD OF LABELLING VIRAL PARTICLES COMPRISING ANIONIC LIPIDS WITH FLUORESCENTLY-LABELLED NEGATIVELY-CHARGED POLYNUCLEOTIDES IN THE PRESENCE OF POLYVALENT CATIONS

(71) Applicant: Oxford University Innovation Limited, Oxford (GB)

(72) Inventors: Nicole Robb, Oxford (GB); Achillefs Kapanidis, Oxford (GB); Jonathan Taylor, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 1229 days.

(21) Appl. No.: 17/289,900

(22) PCT Filed: Oct. 30, 2019

(86) PCT No.: PCT/GB2019/053073
§ 371 (c)(1),
(2) Date: Apr. 29, 2021

(87) PCT Pub. No.: WO2020/089621
PCT Pub. Date: May 7, 2020

(65) Prior Publication Data
US 2022/0003767 A1     Jan. 6, 2022

(30) Foreign Application Priority Data
Oct. 31, 2018    (GB) ...................................... 1817802

(51) Int. Cl.
*G01N 33/58* (2006.01)
*C12N 7/00* (2006.01)
(Continued)

(52) U.S. Cl.
CPC ............. *G01N 33/582* (2013.01); *C12N 7/00* (2013.01); *C12Q 1/68* (2013.01); *C12Q 1/70* (2013.01);
(Continued)

(58) Field of Classification Search
CPC ............................ C12Q 1/68; C12Q 2525/00; C12Q 2563/107; G01N 33/582; G01N 33/586;
(Continued)

(56) References Cited

FOREIGN PATENT DOCUMENTS

| | | |
|---|---|---|
| WO | 97/05264 A1 | 2/1997 |
| WO | 2016/156878 A1 | 10/2016 |

OTHER PUBLICATIONS

Kapoor, M., and D. J. Burgess, 2012, Efficient and safe delivery of siRNA using anionic lipids: Formulation optimization studies, Intl. J. Pharmaceutics 432:80-90.*
(Continued)

*Primary Examiner* — Jeffrey S Parkin
(74) *Attorney, Agent, or Firm* — Thomas|Horstemeyer, LLP

(57) ABSTRACT
Provided herein is a method of functionalizing a particle, as well as methods of optically tracking a particle, isolating enveloped viral particles from a sample, quantifying enveloped virus particles in a sample and assessing enveloped viral aggregation in a sample. Kits are also provided. The particle is typically a viral particle.

17 Claims, 18 Drawing Sheets

Specification includes a Sequence Listing.

(51) Int. Cl.
  *C12Q 1/68*  (2018.01)
  *C12Q 1/70*  (2006.01)
  *G01N 33/569*  (2006.01)

(52) U.S. Cl.
  CPC ..... *G01N 33/569* (2013.01); *G01N 33/56983* (2013.01); *G01N 33/586* (2013.01); *C12N 2310/3517* (2013.01); *C12N 2760/16121* (2013.01); *C12N 2760/16131* (2013.01); *C12N 2760/16151* (2013.01); *C12N 2760/16221* (2013.01); *C12N 2760/16232* (2013.01); *C12N 2760/16251* (2013.01); *C12Q 2525/00* (2013.01); *C12Q 2563/107* (2013.01)

(58) Field of Classification Search
  CPC .................. G01N 33/569; C12N 15/00; C12N 2310/3517; C12N 2405/00
  See application file for complete search history.

(56) References Cited

OTHER PUBLICATIONS

European Communication for Application No. 19 798 121.0, dated Jan. 16, 2023, pp. 1-7.

Zong-Qiang Cui et al: "Quantum dot-aptamer nanoprobes for recognizing and labeling influenza A virus particles", NANOSCALE, vol. 3, No. 6, Jan. 1, 2011 (Jan. 1, 2011), p. 2454, XP055240164.
International Search Report and Written Opinion for WO 2020/089621 (PCT/GB2019/053073), dated Feb. 25, 2020, pp. 1-18.
UK Search Report for GB 1817802.0, dated Jun. 21, 2019, pp. 1-5.
Mohammed Saifuddin et al: "Interaction of mannose-binding lectin with primary isolates of human Immunodeficiency virus type I", Journal of General Virology., vol. 81, No. 4, Apr. 1, 2000 (Apr. 1, 2000), pp. 949-955.
G. D. Gaiha et al: "Surfactant Protein A Binds to HIV and Inhibits Direct Infection of CD4+ Cells, but Enhances Dendritic Cell-Mediated Viral Transfer", The Journal of Immunology, vol. 181, No. 1. Jun. 19, 2008 (Jun. 19, 2008) pp. 601-609.
European Communication for Application No. 19 798 121.0, dated Aug. 29, 2022, pp. 1-4.
Mamta et al: "Cellular Uptake Mechanisms of Novel Anionic siRNA Lipoplexes", Pharmaceutical Research, vol. 30, No. 4, Apr. 1, 2013, pp. 1161-1175, XP055954355.
Mamta et al: "Efficient and safe delivery of siRNA using anionic lipids: Formulation of optimization studies", International Journal of Pharmaceutics, vol. 432, No. 1, Apr. 21, 2012, pp. 80-90, XP028510750.

* cited by examiner

A

B

C

Exosomes
CaCl₂
DNA

FOV (532nm)

Merged localisations

Non-filtered

Filtered

Negative

SEQUENCE LISTING

```
<160> NUMBER OF SEQ ID NOS: 21

<210> SEQ ID NO 1
<211> LENGTH: 26
<212> TYPE: PRT
<213> ORGANISM: Artificial Sequence
<220> FEATURE:
<223> OTHER INFORMATION: Immobilization tag (calmodulin tag)

<400> SEQUENCE: 1

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 2
<211> LENGTH: 13
<212> TYPE: PRT
<213> ORGANISM: Artificial Sequence
<220> FEATURE:
<223> OTHER INFORMATION: Immobilization tag (E-tag)

<400> SEQUENCE: 2

Gly Ala Pro Val Pro Tyr Pro Asp Pro Leu Glu Pro Arg
1               5                   10

<210> SEQ ID NO 3
<211> LENGTH: 8
<212> TYPE: PRT
<213> ORGANISM: Artificial Sequence
<220> FEATURE:
<223> OTHER INFORMATION: Immobilization tag (FLAG-tag)

<400> SEQUENCE: 3

Asp Tyr Lys Asp Asp Asp Asp Lys
1               5
```

-continued

```
<210> SEQ ID NO 4
<211> LENGTH: 9
<212> TYPE: PRT
<213> ORGANISM: Artificial Sequence
<220> FEATURE:
<223> OTHER INFORMATION: Immobilization tag (HA-tag)

<400> SEQUENCE: 4

Tyr Pro Tyr Asp Val Pro Asp Tyr Ala
1               5

<210> SEQ ID NO 5
<211> LENGTH: 10
<212> TYPE: PRT
<213> ORGANISM: Artificial Sequence
<220> FEATURE:
<223> OTHER INFORMATION: Immobilization tag (Myc-tag)

<400> SEQUENCE: 5

Glu Gln Lys Leu Ile Ser Glu Glu Asp Leu
1               5                   10

<210> SEQ ID NO 6
<211> LENGTH: 18
<212> TYPE: PRT
<213> ORGANISM: Artificial Sequence
<220> FEATURE:
<223> OTHER INFORMATION: Immobilization tag (NE-tag)

<400> SEQUENCE: 6

Thr Lys Glu Asn Pro Arg Ser Asn Gln Glu Glu Ser Tyr Asp Asp Asn
1               5                   10                  15

Glu Ser

<210> SEQ ID NO 7
<211> LENGTH: 15
<212> TYPE: PRT
<213> ORGANISM: Artificial Sequence
<220> FEATURE:
<223> OTHER INFORMATION: Immobilization tag (S-tag)

<400> SEQUENCE: 7

Lys Glu Thr Ala Ala Ala Lys Phe Glu Arg Gln His Met Asp Ser
1               5                   10                  15

<210> SEQ ID NO 8
<211> LENGTH: 38
<212> TYPE: PRT
<213> ORGANISM: Artificial Sequence
<220> FEATURE:
<223> OTHER INFORMATION: Immobilization tag (SBP-tag)

<400> SEQUENCE: 8

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 9
<211> LENGTH: 12
<212> TYPE: PRT
<213> ORGANISM: Artificial Sequence
```

```
<220> FEATURE:
<223> OTHER INFORMATION: Immobilization tag (Spot-tag)

<400> SEQUENCE: 9

Pro Asp Arg Val Arg Ala Val Ser His Trp Ser Ser
1               5                   10

<210> SEQ ID NO 10
<211> LENGTH: 8
<212> TYPE: PRT
<213> ORGANISM: Artificial Sequence
<220> FEATURE:
<223> OTHER INFORMATION: Immoblization tag (Strep-tag)

<400> SEQUENCE: 10

Trp Ser His Pro Gln Phe Glu Lys
1               5

<210> SEQ ID NO 11
<211> LENGTH: 6
<212> TYPE: PRT
<213> ORGANISM: Artificial Sequence
<220> FEATURE:
<223> OTHER INFORMATION: Immobilization tag (TC tag)

<400> SEQUENCE: 11

Cys Cys Pro Gly Cys Cys
1               5

<210> SEQ ID NO 12
<211> LENGTH: 10
<212> TYPE: PRT
<213> ORGANISM: Artificial Sequence
<220> FEATURE:
<223> OTHER INFORMATION: Immobilization tag (Ty tag)

<400> SEQUENCE: 12

Glu Val His Thr Asn Gln Asp Pro Leu Asp
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Immobilization tag (V5 tag)

<400> SEQUENCE: 13

Gly Lys Pro Ile Pro Asn Pro Leu Leu Gly Leu Asp Ser Thr
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Immobilization tag (VSV tag)

<400> SEQUENCE: 14

Tyr Thr Asp Ile Glu Met Asn Arg Leu Gly Lys
1               5                   10

<210> SEQ ID NO 15
<211> LENGTH: 8
<212> TYPE: PRT
<213> ORGANISM: Artificial Sequence
<220> FEATURE:
```

<223> OTHER INFORMATION: Immobilization tag (Xpress tag)

<400> SEQUENCE: 15

Asp Leu Tyr Asp Asp Asp Asp Lys
1               5

<210> SEQ ID NO 16
<211> LENGTH: 16
<212> TYPE: PRT
<213> ORGANISM: Artificial Sequence
<220> FEATURE:
<223> OTHER INFORMATION: Immobilization tag (Isopeptag)

<400> SEQUENCE: 16

Thr Asp Lys Asp Met Thr Ile Thr Phe Thr Asn Lys Lys Asp Ala Glu
1               5                   10                  15

<210> SEQ ID NO 17
<211> LENGTH: 13
<212> TYPE: PRT
<213> ORGANISM: Artificial Sequence
<220> FEATURE:
<223> OTHER INFORMATION: Immobilization tag (SpyTag)

<400> SEQUENCE: 17

Ala His Ile Val Met Val Asp Ala Tyr Lys Pro Thr Lys
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Immobilization tag (SnoopTag)

<400> SEQUENCE: 18

Lys Leu Gly Asp Ile Glu Phe Ile Lys Val Asn Lys
1               5                   10

<210> SEQ ID NO 19
<211> LENGTH: 64
<212> TYPE: DNA
<213> ORGANISM: Artificial Sequence
<220> FEATURE:
<223> OTHER INFORMATION: Single-stranded oligonucleotide
<220> FEATURE:
<221> NAME/KEY: misc_feature
<222> LOCATION: (64)..(64)
<223> OTHER INFORMATION: T-Atto647N

<400> SEQUENCE: 19
gaaattgtta tccgctctca caattccaca cattatacga gccgaagcat aaagtgtcaa      60
gcct                                                                  64

<210> SEQ ID NO 20
<211> LENGTH: 64
<212> TYPE: DNA
<213> ORGANISM: Artificial Sequence
<220> FEATURE:
<223> OTHER INFORMATION: Single-stranded oligonucleotide
<220> FEATURE:
<221> NAME/KEY: misc_feature
<222> LOCATION: (25)..(25)
<223> OTHER INFORMATION: T-Cy3B

<400> SEQUENCE: 20
aggcttgaca ctttatgctt cggctcgtat aatgtgtgga attgtgagag cggataacaa      60

-continued

```
tttc                                                       64

<210> SEQ ID NO 21
<211> LENGTH: 34
<212> TYPE: RNA
<213> ORGANISM: Artificial Sequence
<220> FEATURE:
<223> OTHER INFORMATION: Single-stranded oligonucleotide
<220> FEATURE:
<221> NAME/KEY: misc_feature
<222> LOCATION: (18)..(18)
<223> OTHER INFORMATION: U-Cy3

<400> SEQUENCE: 21
aguagaaaca aggaguuuuu ugaacaaacu acuu                      34
```

METHOD OF LABELLING VIRAL PARTICLES COMPRISING ANIONIC LIPIDS WITH FLUORESCENTLY-LABELLED NEGATIVELY-CHARGED POLYNUCLEOTIDES IN THE PRESENCE OF POLYVALENT CATIONS

CROSS-REFERENCE TO RELATED APPLICATIONS

This application is the National Stage of International Application No. PCT/GB2019/053073, filed Oct. 30, 2019, which claims priority to GB 1817802.0, filed Oct. 31, 2018, which are entirely incorporated herein by reference.

SEQUENCE LISTING

This application contains a sequence listing filed in ST.25 format entitled "pctgb2019053073-seq1.txt" created on Oct. 3, 2025, and having a size of 5,562 bytes. The entire content of the sequence listing is incorporated herein in its entirety as if fully set forth herein.

FIELD OF THE INVENTION

The invention relates to methods of functionalizing particles. Specifically, the method relates to methods of functionalizing a particle with a negatively charged polymer. The particle has a negatively charged surface and the polymer also has a negatively charged portion. The invention also relates to functionalized particles obtainable by the methods of the invention. The invention further relates to methods of optically tracking a particle; to methods of functionalizing the surface of a particle with a reactive functional group; to methods of isolating enveloped viral particles from a sample; and to methods of assessing enveloped viral aggregation in a sample. The invention also relates to kits for conducting such methods. The particle is typically an enveloped virus particle.

BACKGROUND OF THE INVENTION

Detection of viruses is an essential requirement for diagnostic tests.

Infectious diseases caused by viruses represent a huge global public health concern, causing many thousands of deaths annually. Notable human diseases caused by viruses include HIV, influenza, Ebola haemorrhagic fever, hepatitis C, dengue, Zika, measles and rabies. Influenza alone results in the deaths of up to 650,000 people every year during annual epidemics, with higher death rates recorded during more severe intermittent pandemics such as the 1918 Spanish flu pandemic that killed more than 50 million people worldwide. In spite of the high mortality rates associated with these viruses, we do not currently have a fully effective toolkit of diagnostic assays to detect and identify these dangerous pathogens.

Rapid viral diagnosis is important for the provision of strain-specific antiviral treatment; particularly as antiviral compounds can often be expensive or toxic. As well as providing targeted therapy, early detection of viruses can also provide a longer treatment window, resulting in reduced treatment costs and morbidity, help prevent transmission, and lead to more efficient disease management and control. There is thus a clear need for methods which allow the rapid detection and identification of viruses.

Traditionally, the gold standard for viral detection has been virus culture in eukaryotic cell lines, which is extremely sensitive but takes significant time (7-10 days). Alternative nucleic acid amplification techniques like RT-PCR are also commonly used, which are highly specific and sensitive but take several hours to obtain a result. These conventional techniques cannot provide the necessary information in an acceptable timeframe.

Some attempts have been made to overcome these difficulties, but none have been entirely successful. For example, antigen-based rapid diagnostic tests that use antibodies to target viral proteins are available for a small subset of viruses such as influenza and respiratory syncytial virus (RSV). Although these tests are relatively quick (typically taking less than 30 minutes), they are limited by variable detection sensitivity (i.e. the proportion of positive cases that are correctly identified, this can be as low as 62.3%) and large numbers of false positives or negatives due to variations in viral load or the improper use of swabs. Furthermore, these methods are only suitable for use in identifying viruses for which appropriate antibodies are available.

Other attempts have been based on the direct quantification and identification of intact virus particles. Flow cytometry-based virus quantification was first described for baculovirus particles and has since been used to quantify a variety of other viruses with differing morphologies and genome sizes. However, such techniques make use of fluorescent dyes that bind non-specifically to viral DNA or RNA such as SYBR Green 1 or DAPI, or to viral proteins, all of which require at least a 30 minute incubation period for efficient virus labelling prior to virus quantification. Improved methods are still required.

Yet other attempts have focused on the use of microscopy. Whilst most viruses are too small to be visualized directly by conventional light microscopy, direct negative stain transmission electron microscopy (TEM) images have been used since the 1940s as an important tool to image individual virus particles and quantitatively determine virus concentrations. However, due to the high costs and amount of space required for a TEM instrument this is still only available in certain facilities.

There is thus an urgent need for detection methods that meet the criteria of being easy to use, sensitive, specific, rapid and cheap. The methods of the present invention address some or all of these technical problems.

SUMMARY OF THE INVENTION

The present inventors have surprisingly found that particles having a negatively charged surface can be functionalized with negatively charged polymers by contacting the particles with (i) a polyvalent cation and (ii) the polymer; such that the polymer binds to the particle thereby functionalizing the particle. As described in more detail herein, the inventors have shown that using such methods particles such as viral particles can be very rapidly and reproducibly functionalized. Sample sensitivity is extremely high and the methods are robust and widely applicable. By appropriate design of the polymer used to functionalize the particle, optical detection and/or tracking of the particle is possible, and the methods can thus be used to quantify parameters such as the amount of virus particles in a sample or the extent of viral aggregation. The methods are particularly suited to the functionalization, detection and quantification of enveloped virus particles, but are not limited to such particles, and are widely applicable.

The invention therefore provides a method of functionalizing a particle with a negatively charged polymer; the particle having a negatively charged surface and a lipid coating; wherein the method comprises contacting said particle with (i) a polyvalent cation and (ii) said polymer; such that the polymer binds to the particle thereby functionalizing the particle.

The method of the invention has several advantages over existing detection techniques. For example, when the particle is a virus, the virus could be detected directly in complex biological fluids such as MEM or allantoic fluid from eggs, without the need for purification or amplification steps. The labelling was instantaneous and the signal from diffusing fluorescent viruses could be observed and analysed very rapidly, e.g. in about a minute. This timescale is significantly shorter than the conventionally used fluorescent dyes used to label viruses for flow cytometry, which require an incubation period of at least 30 minutes. In addition, the technique is simple and cost-effective, and does not require expensive reagents. Only a small sample volume is required. Furthermore, once functionalised, virus particles could be detected at a very low concentration.

The invention also provides a functionalized particle which is obtainable by the method of the invention.

The invention further provides a functionalized particle, comprising:
> a particle having a negatively charged surface and a lipid coating;
> a negatively charged polymer; and
> a polyvalent cation which binds the polymer to the particle.

The invention still further provides a composition comprising a functionalized particle according to the invention and a carrier medium.

> Also provided is:
> a method of binding a functionalized virus particle to a host cell, which method comprises binding to a host cell a functionalized particle according to the invention; wherein the particle is an enveloped virus particle;
> a method of releasing a polymer from a functionalized particle according to the invention, which method comprises contacting the functionalized particle with a chelating agent for the polyvalent cation;
> a method of optically tracking a particle having a negatively charged surface and a lipid coating; the method comprising:
> a) functionalizing the particle with a negatively charged polymer by a method according to the invention, wherein the negatively charged polymer comprises an optically detectable label; and
> b) optically tracking the optically detectable label thereby tracking the particle; wherein preferably the particle is an enveloped viral particle.
> a method of functionalizing the surface of a particle having a negatively charged surface and a lipid coating; the method comprising functionalizing the particle with a negatively charged polymer according to the invention; wherein the negatively charged polymer comprises one or more reactive functional groups; such that the polymer binds to the surface of the particle thereby functionalizing the surface of the particle; wherein preferably the particle is an enveloped viral particle;
> a method of isolating enveloped viral particles from a sample, comprising:
> a) functionalizing the enveloped viral particles in the sample with a negatively charged polymer according to the invention; wherein the negatively charged polymer comprises an immobilization tag;
> b) contacting the immobilization tag with a substrate therefor such that the immobilization tag binds to the substrate;
> c) isolating the substrate from the sample; and
> d) optionally releasing the viral particles from the substrate.
> a method of quantifying enveloped virus particles in a sample, comprising:
> a) functionalizing the enveloped viral particles in the sample with a negatively charged polymer according to the invention; wherein the negatively charged polymer comprises a detectable label;
> b) detecting the detectable label; and
> c) determining the number or concentration of detectable labels in the sample thereby quantifying the number or concentration of labelled viral particles in the sample.
> a method of assessing enveloped viral aggregation in a sample, comprising:
> a) functionalizing the enveloped viral particles in the sample with a negatively charged polymer according to the invention; wherein the negatively charged polymer comprises an optically detectable label; wherein the individual viruses in the population have a known size;
> b) optically tracking motion of the labelled viral particles;
> c) determining an average diffusion coefficient for the labelled viral particles in the sample and thereby obtaining an estimate of the particulate size of the labelled viral particles;
> d) comparing the known size of the viruses in the population with the estimated particulate size of the labelled viral particles and thereby assessing the extent of viral aggregation in the sample and
> a kit comprising:
> (i) a particle having a negatively charged surface and a lipid coating;
> (ii) a negatively charged polymer; and
> (iii) a polyvalent cation for binding the polymer to the particle.

BRIEF DESCRIPTION OF THE FIGURES

FIG. 1A shows a schematic representation of the assay; where fluorescent DNAs are used to non-specifically label diffusing virus particles. Multiply-labelled viruses are very bright, and move slowly, while free DNA is less bright and diffuses much more quickly. Samples are observed using wide-field variable-angle epifluorescence microscopy (VAEM). FIG. 1B shows how by localizing visible peaks and associating nearby localizations in subsequent frames with each other the two-dimensional paths of molecules are reconstructed for the duration of their visibility in the focal plane. In FIG. 1C the diffusion coefficients of the tracked particles are plotted on a histogram and the mean diffusion coefficient ($D_m$) is used to give an estimate of the average size of the diffusing molecules ($d_{st}$) using the Stokes-Einstein relation. FIG. 1D shows a representative field-of-view of fluorescently-labelled influenza virus diffusing in solution. A/Puerto Rico/8/1934 (H1N1) virus at a final concentration of $5.25 \times 10^6$ PFU/mL was added to 0.65M $CaCl_2$ and 1 nM Atto647N-labelled DNA before being observed using a wide-field microscope. Scale bar 10 μm. Circles represent examples of localised particles. FIG. 1E shows representative tracks from the first 200 frames of the acquisition movie for fluorescently-labelled influenza virus diffusing in solution. Scale bar 10 µm. FIG. 1F shows a diffusion coefficient histogram for A/Puerto Rico/8/1934. n=Number of tracks. Also shown are negative controls where virus was replaced with water (FIG. 1G) or minimal essential media (FIG. 1H); negative controls where $CaCl_2$ (FIG. 1I) or DNA (FIG. 1J) were replaced with water. FIG. 1K shows how addition of 100 mM of the calcium chelator EDTA to the imaging well resulted in the loss of signal.

FIG. 2A: Timeline of experiment. Virus was added to a $CaCl_2$ and DNA solution at time 0, the mixture was then immediately placed in a well of a glass slide on the microscope, and imaged. An acquisition movie of 1000 frames, taken at a frame rate of 30 Hz, was then taken, followed by data analysis (typically 20 seconds). FIG. 2B: A/Puerto Rico/8/1934 virus at a final concentration of $2.625 \times 10^7$ PFU/mL was added to 0.65M $CaCl_2$ and 1 nM Atto647N-labelled DNA and incubated for 1, 6, 15 or 20 minutes before being observed. The dotted line represents the minimal number of tracks (400) required for effective virus detection. FIG. 2C: Representative fields-of-view from graph B. Scale bar 10 µm. FIG. 2D: A/Puerto Rico/8/1934 virus at a final concentration of $2.625 \times 10^7$ PFU/mL was added to 0.65M $CaCl_2$ and either 0, 0.1, 1 or 10 nM Atto647N-labelled DNA before being observed using a wide-field microscope. FIG. 2E: A/Puerto Rico/8/1934 virus at a final concentration of $2.625 \times 10^7$ PFU/mL was added to 0, 0.02, 0.09, 0.18, 0.35 or 0.7M $CaCl_2$ and 1 nM Atto647N-labelled DNA. FIG. 2F: Increasing concentrations of virus (0, $0.5 \times 10^6$, $2.6 \times 10^6$, $5.3 \times 10^6$ or $26.3 \times 10^6$ PFU/mL) were added to 0.65M $CaCl_2$ and 1 nM Atto647N-labelled DNA.

FIG. 3A: Number of tracks observed in a 1000 frame acquisition when A/Puerto Rico/8/1934 (H1N1) virus at a final concentration of $26.25 \times 10^6$ PFU/mL was added to 1 nM Atto647N-labelled DNA and either 0.65M KCl, NaCl, $MgCl_2$, $CaCl_2$ or 0.32M spermine. FIG. 3B: Number of tracks observed in a 1000 frame acquisition when 1 nM fluorescently-labelled DNA was replaced with 1 nM Cy3B-labelled RNA, 1 nM fluorescently-labelled protein (DNA polymerase) or 1 nM free Atto647N dye. FIG. 3C: Number of tracks observed in a 1000 frame acquisition when $3.3 \times 10^{11}$ PFU/mL adenovirus was added to 1 nM Atto647N-labelled DNA and 0.65M $CaCl_2$ before being observed, or when virus was replaced with 200 nm anionic, cationic or neutral charged lipid vesicles.

FIG. 4A: Representative field-of-view of fluorescently-labelled A/WSN/33 influenza virus diffusing in solution. Virus at a final concentration of $49.5 \times 10^6$ PFU/mL was added to 0.65M $CaCl_2$, 1 nM Atto647N-labelled DNA and 0.0025× trypsin before being observed using a wide-field microscope. Scale bar 10 µm. FIG. 4B: Diffusion coefficient histogram for A/WSN/33. n=Number of tracks. FIGS. 4C and 4D: As for FIGS. 4A and 4B but for A/X31 virus. Virus at a final concentration of $22.5 \times 10^6$ PFU/mL was added to 0.65M $CaCl_2$, 1 nM Atto647N-labelled DNA and 0.0025× trypsin before being observed using a wide-field microscope. FIGS. 4E and 4F: As for FIGS. 4A and 4B but for B/Florida/04/2006. Virus at a final concentration of $3.15 \times 10^6$ PFU/mL was added to 0.65M $CaCl_2$, 1 nM Atto647N- labelled DNA and 0.0025× trypsin before being observed using a wide-field microscope. Circles represent larger aggregates of virus particles.

Figure 5:
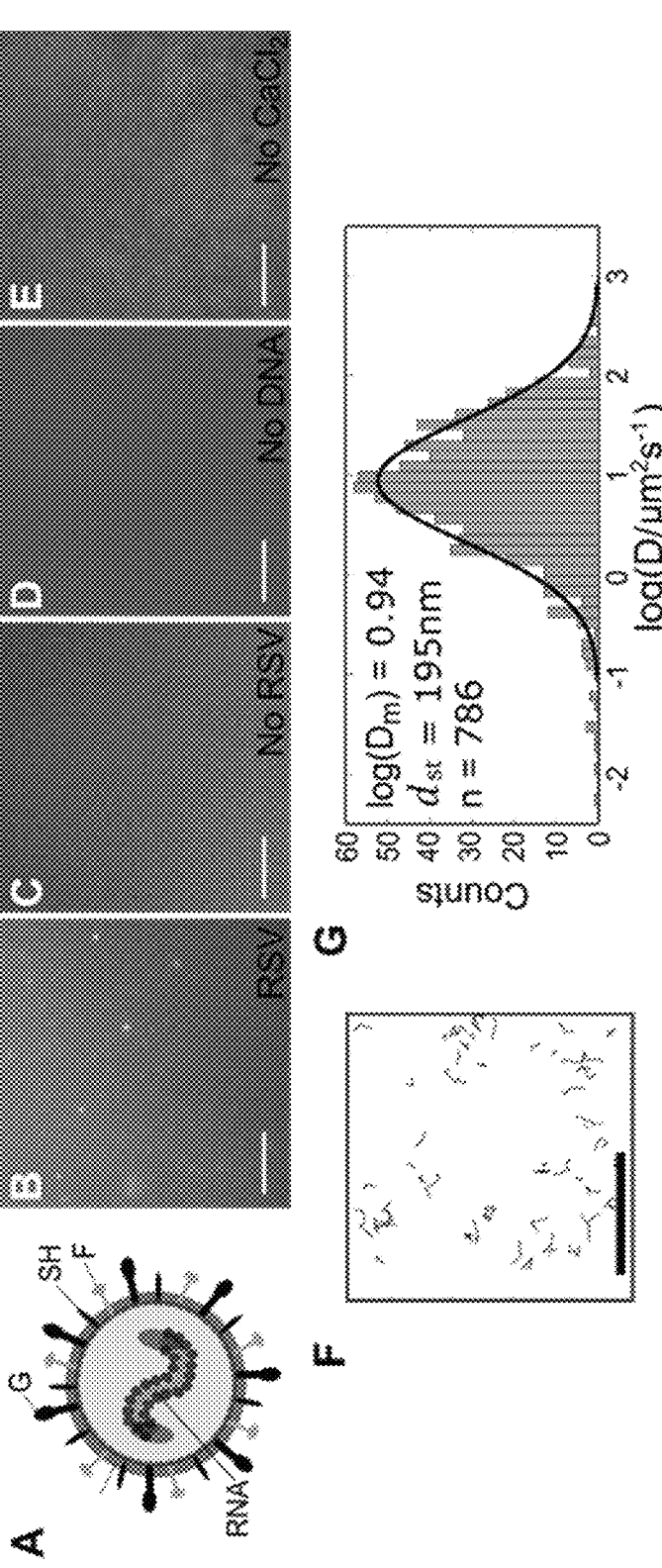

FIG. 5 shows how calcium chloride can be used to fluorescently label respiratory syncytial virus (RSV). FIG. 5A: Schematic representation of an RSV particle. Virus particles have three transmembrane proteins (attachment (G) protein, fusion (F) protein and small hydrophobic (SH) protein), beneath which lies a layer of matrix protein (M), which encloses the single-stranded RNA genome. FIG. 5B: Representative field-of-view of fluorescently-labelled RSV virus diffusing in solution. A2 virus at a final concentration of $7.0 \times 10^2$ PFU/mL was added to 0.7M $CaCl_2$, 1 nM Atto647N-labelled DNA and 0.0025× trypsin before being observed using a wide-field microscope. Scale bar 10 µm. FIG. 5C-5E: Negative controls where virus (FIG. 5C), DNA (FIG. 5D) or $CaCl_2$ (FIG. 5E) were replaced with water were also observed. FIG. 5F: Representative tracks from the first 1000 frames of the acquisition movie for fluorescently-labelled RSV diffusing in solution. Scale bar 10 µm. FIG. 5G: Diffusion coefficient histogram for A2 RSV. n=Number of tracks.

Figure 6:
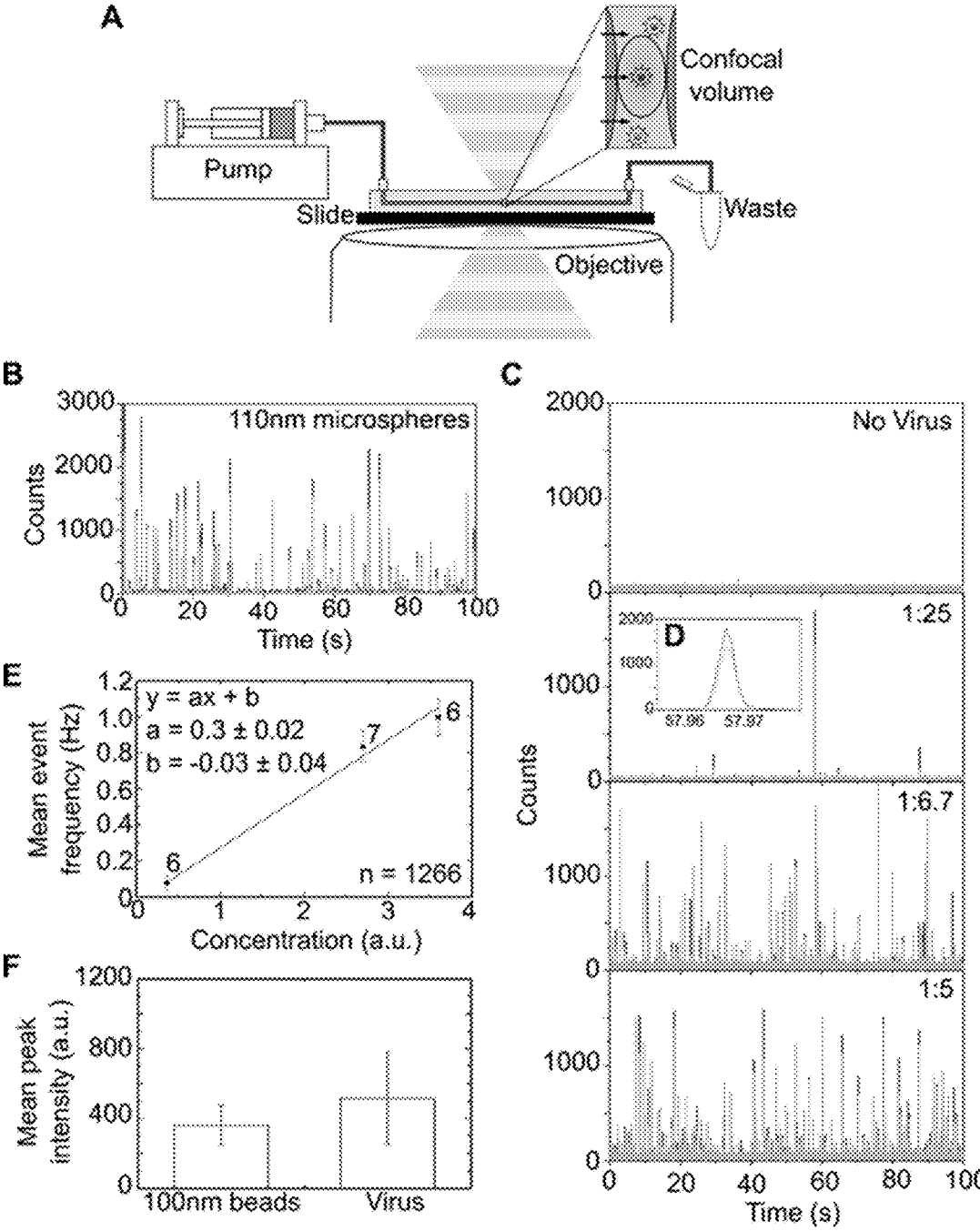

FIG. 6 shows that non-specifically labelled influenza viruses are extremely bright, allowing rapid whole virus quantification. FIG. 6A: Schematic representation of the detection system used. Doubly-labelled viruses were flowed through a microslide channel (100 µm high×1 mm wide) using a syringe infusion pump and illuminated using alternating red (647 nm) and green (532 nm) laser excitation at a modulation frequency of 10 kHz. Bursts of fluorescence corresponding to the passage of each virus particle through the confocal volume were split spectrally onto two avalanche photodiodes detecting red and green fluorescence. Custom-made LabVIEW software was used to register and evaluate the detector signal. FIG. 6B: Detection of 110 nm fluorescent microspheres using the flow detection system. FIG. 6C: A/Puerto Rico/8/1934 virus at a final concentration of $5.25 \times 10^6$ PFU/mL was doubly-labelled with 0.65M $CaCl_2$ and 1 nM Atto647N- and Cy3B-labelled DNA before being flowed through the microslide at increasing concentrations. FIG. 6D: Zoomed in image of a fluorescent burst corresponding to the passage of a virus particle through the confocal volume. FIG. 6E: Plot of mean number of fluorescent events occurring with increasing concentration of labelled virus. The numbers next to each point represent the number of acquisition movies used at each concentration. n=Number of bursts. FIG. 6F: Comparison of mean peak intensities of microspheres and virus particles. Error bars represent the standard deviation of the mean.

Figure 7:
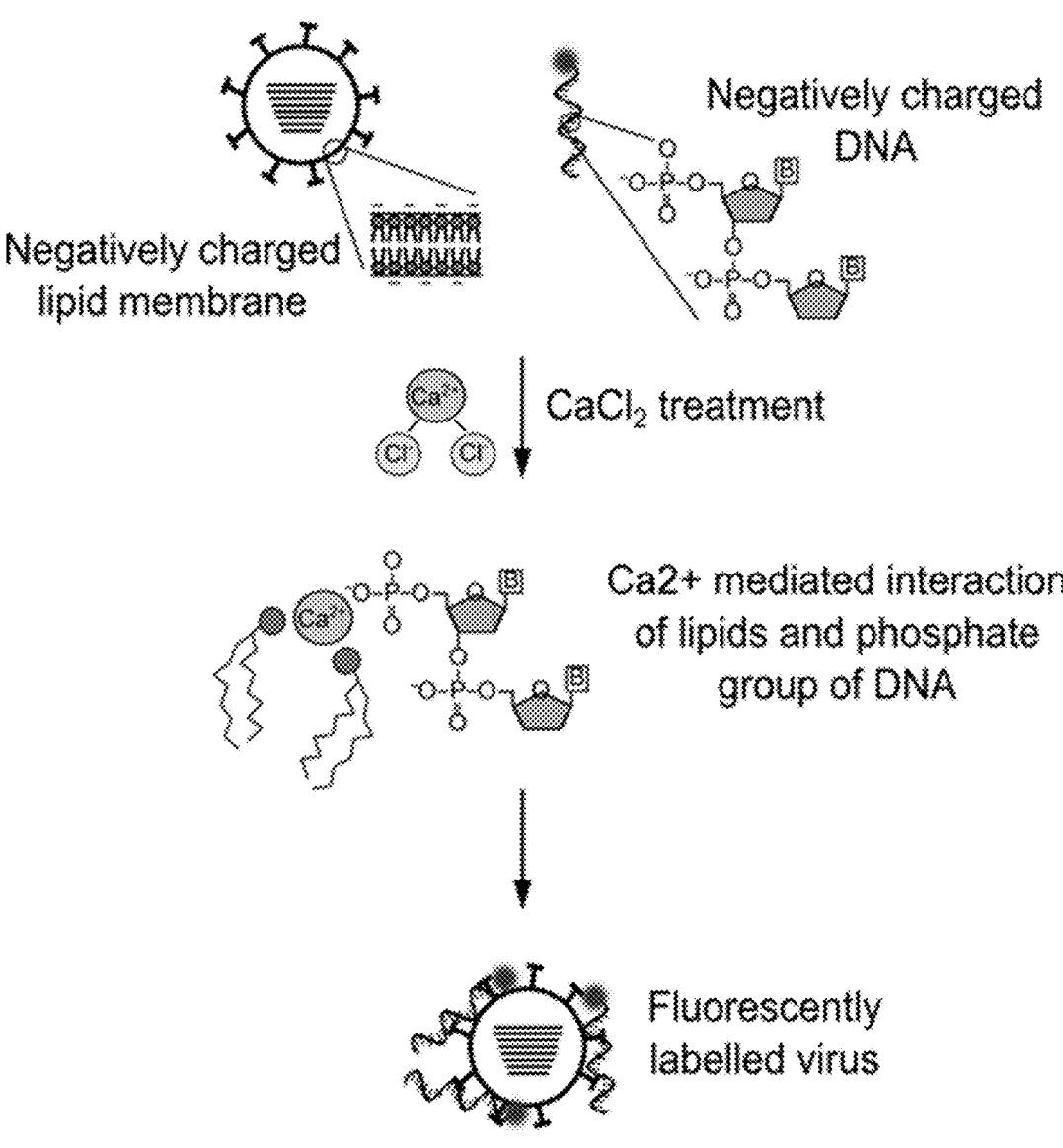

FIG. 7 shows a schematic model of calcium chloride-based fluorescent labelling of viruses. Enveloped viruses have an overall negative charge due to the phospholipids on the cell surface. DNA also has an overall negative charge due to multiple phosphate groups, B=base. Addition of calcium chloride ($CaCl_2$) provides divalent calcium cations that facilitate an interaction between the negatively charged polar heads of the viral lipid membrane and the negatively charged phosphates of the nucleic acid, possibly by binding two lipid molecules and a phosphate at the same time.

Figure 8:

FIG. 8 shows differentiation between fluorescent microspheres of different sizes using single-particle tracking analysis. FIG. 8A: Representative field-of-view of 110 nm fluorescent microspheres diffusing in water. Scale bar 10 µm. FIG. 8B: Representative tracks from the first 200 frames of the acquisition. Scale bar 10 µm. FIG. 8C: Diffusion coefficient histogram for the 110 nm microspheres. n=Number of tracks. FIG. 8D: Representative field-of-view of 46 nm fluorescent microspheres diffusing in water. Scale bar 10 μm. FIG. 8E: Representative tracks from the first 200 frames of the acquisition. Scale bar 10 μm. FIG. 8F: Diffusion coefficient histogram for the 46 nm microspheres. n=Number of tracks.

Figure 9:
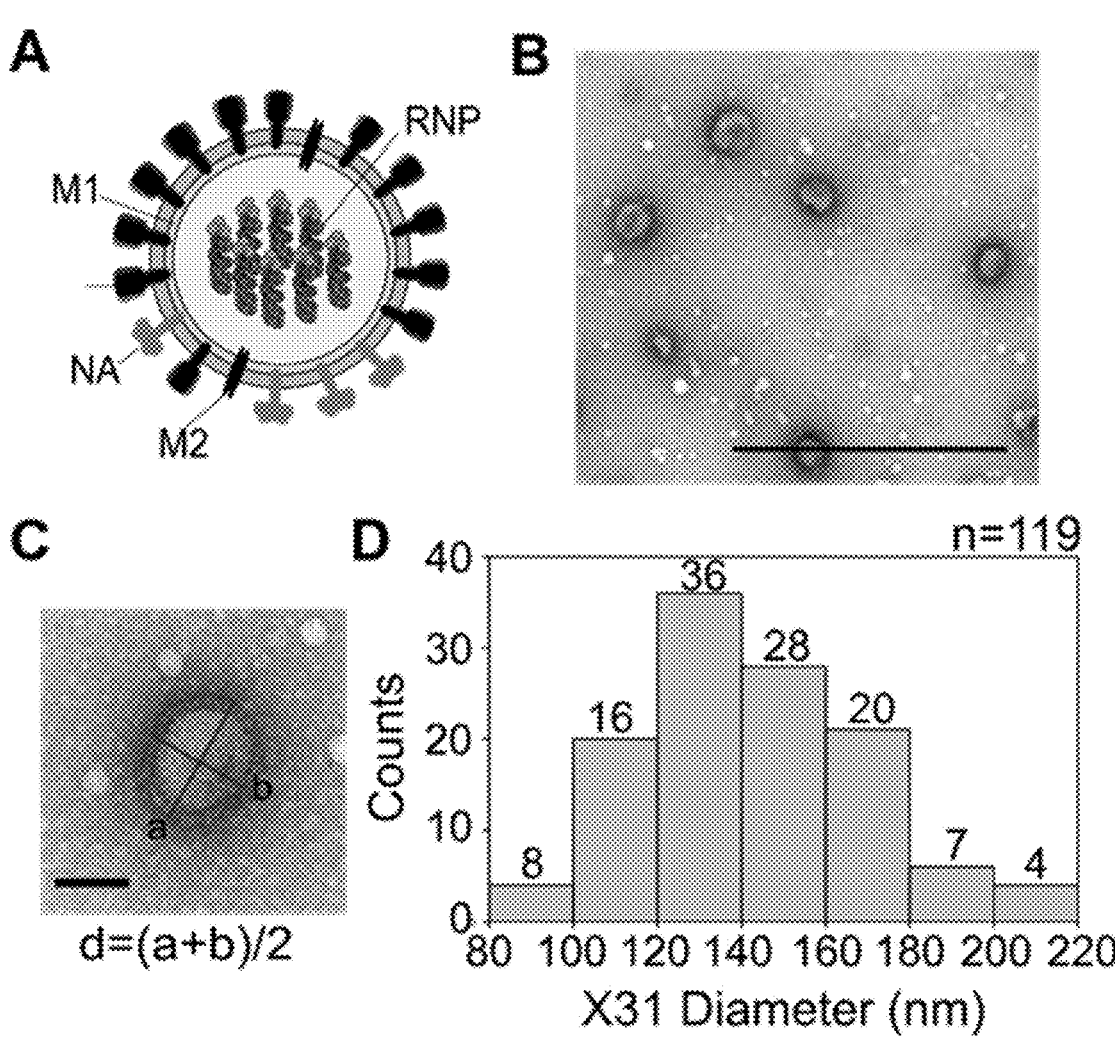

FIG. 9 shows electron microscopy measurement of influenza virus particle size. FIG. 9A: Schematic representation of an influenza particle. Virus particles have three transmembrane proteins (HA, NA and M2), beneath which lies a layer of matrix protein (M1), which encloses the eight genomic ribonucleoproteins (RNPs). FIG. 9B: Representative electron micrograph image of negatively stained X31 influenza particles. Scale bar 1 μm. FIG. 9C: The mean diameter of each virus particle was calculated by taking the average between major and minor axes. Scale bar 0.1 μm. FIG. 9D: Histogram of the mean diameter of the X31 virus. Number of virus particles counted (n)=119.

Figure 10:
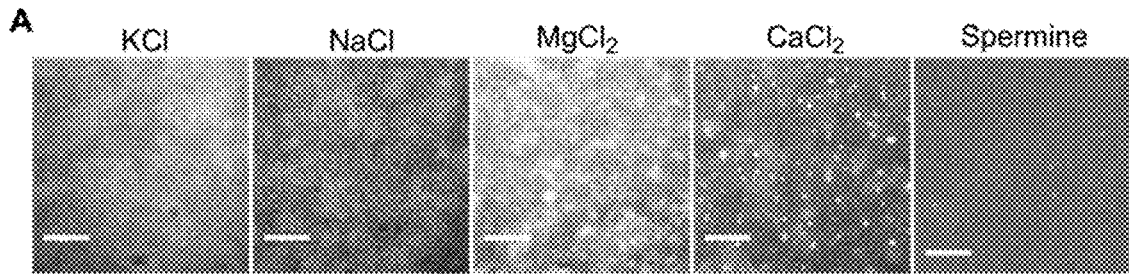
Figure 10:
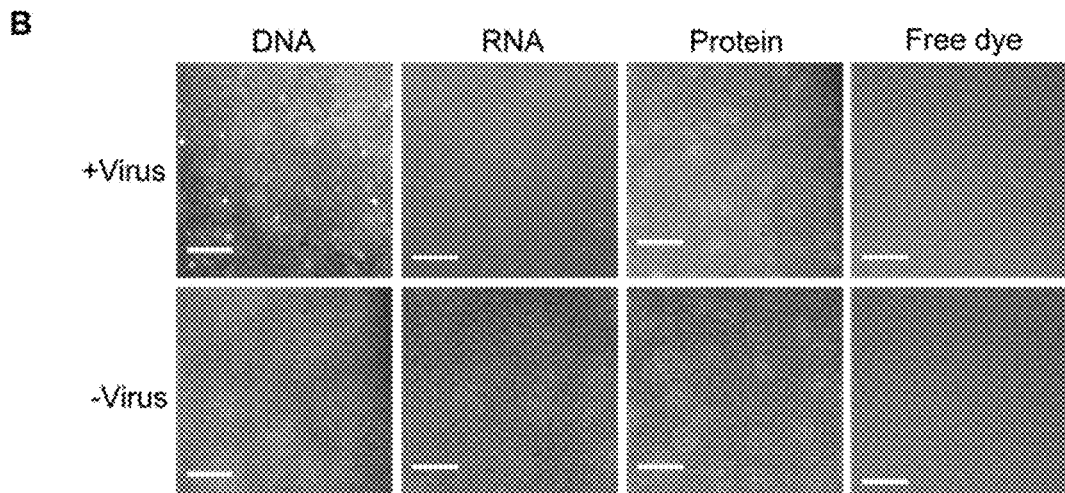
Figure 10:
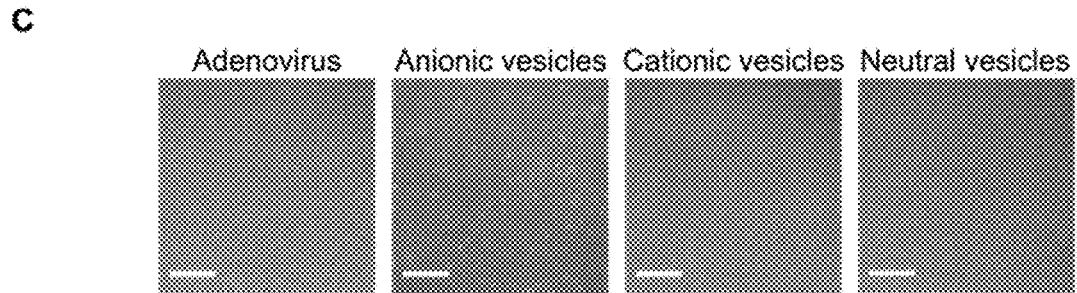

FIG. 10 shows virus labelling using calcium chloride, a fluorescent nucleic acid and a viral envelope. FIG. 10A: Representative fields-of-view when A/Puerto Rico/8/1934 (H1N1) virus at a final concentration of $26.25 \times 10^6$ PFU/mL was added to 1 nM Atto647N-labelled DNA and either 0.65M KCl, NaCl, $MgCl_2$, $CaCl_2$ or 0.32M spermine. FIG. 10B: Representative fields-of-view when 1 nM fluorescently-labelled DNA was replaced with 1 nM fluorescently-labelled RNA, 1 nM fluorescently-labelled protein (DNA polymerase) or 1 nM free Atto647N dye. FIG. 10C: Representative fields-of-view when $3.3 \times 10^{11}$ PFU/mL adenovirus was added to 1 nM Atto647N-labelled DNA and 0.65M $CaCl_2$ before being observed, or when virus was replaced with 200 nm anionic, cationic or neutral charged lipid vesicles. Scale bars are 10 μm.

Figure 11:
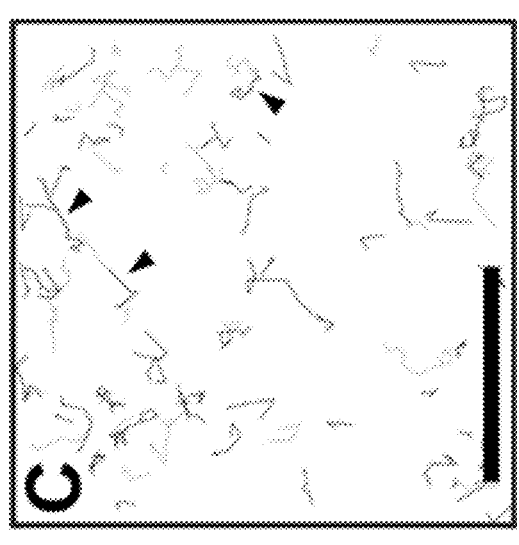
Figure 11:
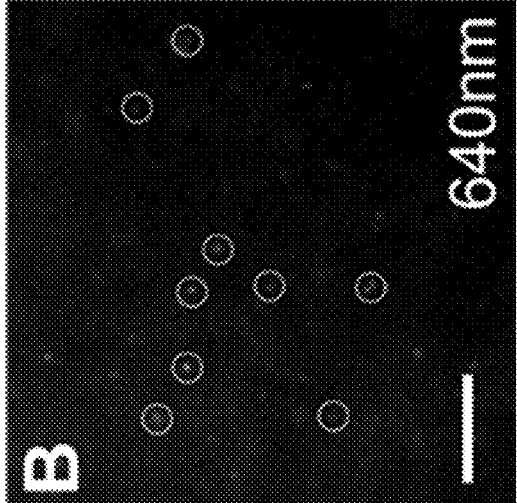
Figure 11:
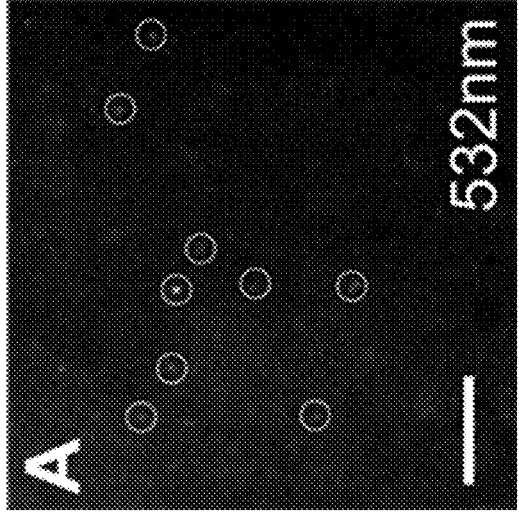

FIG. 11 shows dual-colour labelling and virus tracking with different dyes. FIGS. 11A and 11B: Representative fields-of-view of doubly-labelled influenza viruses diffusing in solution, with FIG. 11A: 532 nm laser illumination and FIG. 11B: 640 nm laser illumination. A/Puerto Rico/8/1934 (H1N1) virus at a final concentration of $5.25 \times 10^6$ PFU/mL was added to 0.65M $CaCl_2$, 1 nM DNA labelled with Atto647N, and 1 nM DNA labelled with Cy3B, before being observed using a wide-field microscope. White circles represent double-labelled particles. Scale bar 10 μm. FIG. 11C: Representative tracks from doubly-labelled viruses. Black arrows show examples of trajectories from double-labelled viruses. Scale bar 10 μm.

Figure 12:
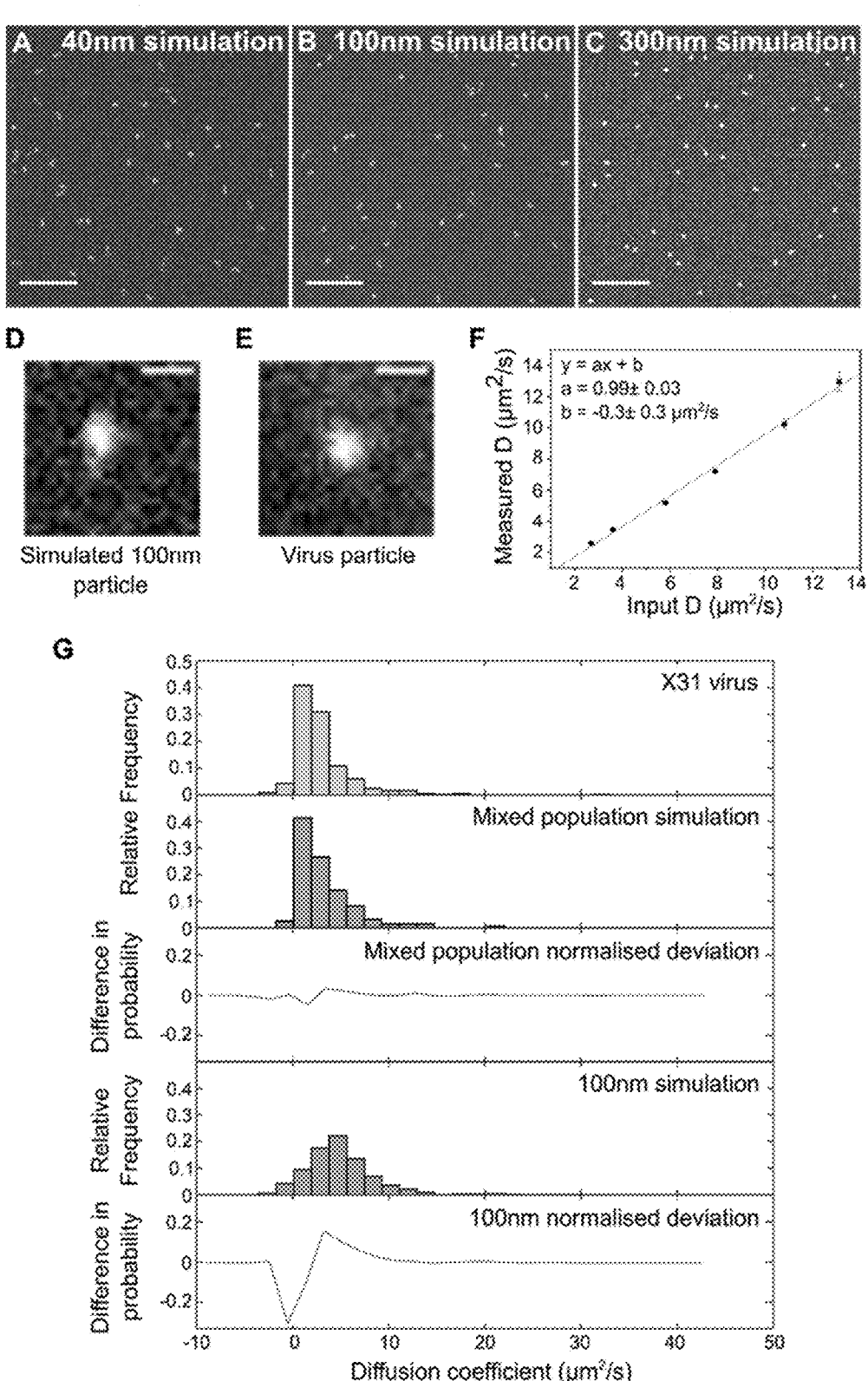

FIG. 12 shows simulations to investigate virus aggregation by characterising the observed motions of a diverse population of diffusing particles of different sizes. FIG. 12A: Representative field-of-view from a simulation movie of 40 nm particles diffusing within a 400×400 pixel area. Scale bar 10 μm. FIG. 12B: Field-of-view from a simulation movie of 100 nm particles. Scale bar 10 μm. FIG. 12C: Field-of-view from a simulation movie of 300 nm particles. Scale bar 10 μm. FIG. 12D: Representative 100 nm particle from a simulated movie. Scale bar 5 μm. FIG. 12E: Zoomed in image of a fluorescently-labelled A/WSN/33 influenza virus diffusing in solution. Virus at a final concentration of $49.5 \times 10^6$ PFU/mL was added to 0.65M $CaCl_2$, 1 nM Atto647N-labelled DNA and 0.0025× trypsin before being observed using a wide-field microscope. Scale bar 5 μm. FIG. 12F: Simulation input diffusion coefficients and the values measured by the software were consistent within error. FIG. 12G: Diffusion coefficient plots from the experimental (X31 virus) and simulated data (mixed population of 100 nm, 200 nm, 300 nm and 400 nm particles, or 100 nm particles only) and differences in mean deviation.

Figure 13:
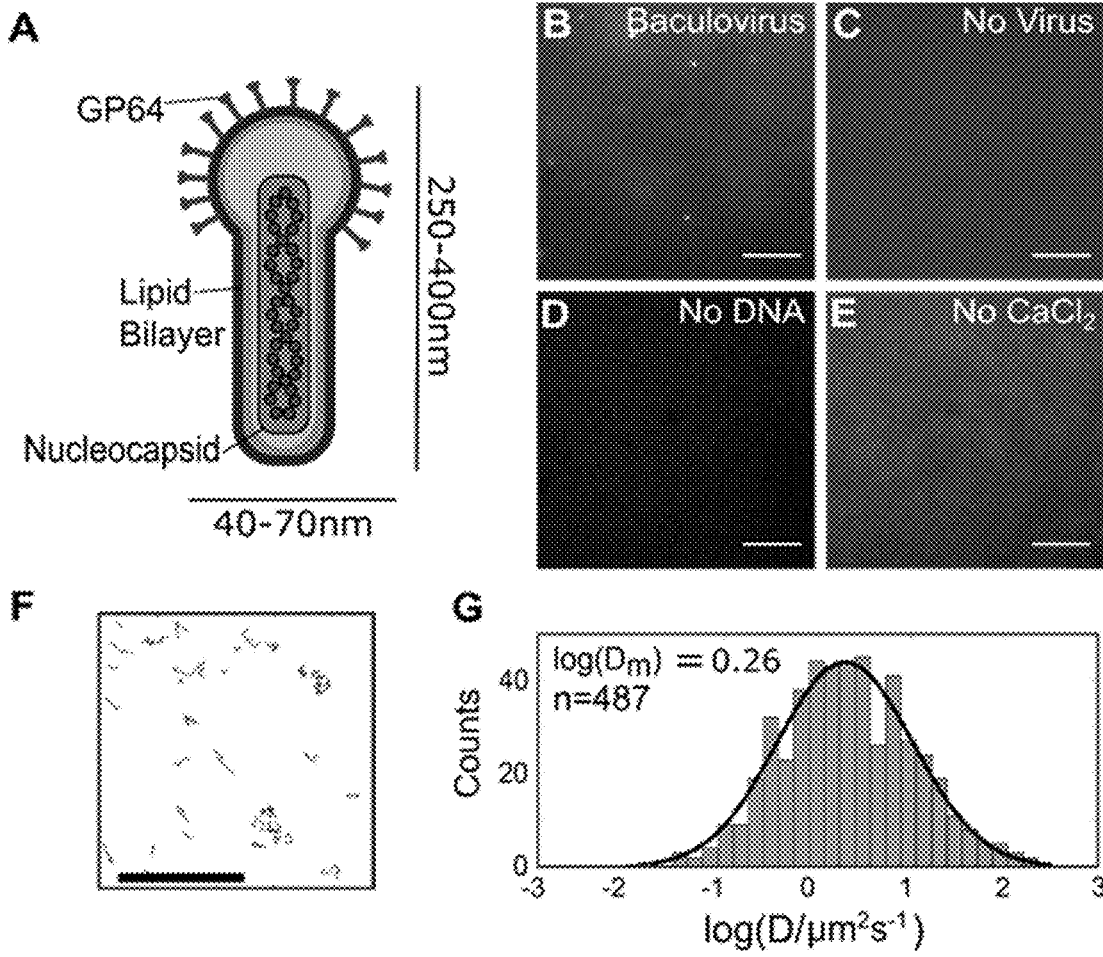

FIG. 13 shows how calcium chloride can be used to fluorescently label baculovirus particles. FIG. 13A: Schematic representation of a baculovirus particle. Virus particles are rod-shaped, with a single transmembrane protein (GP64), beneath which lies a nucleocapsid which encloses the circular double-stranded DNA genome. FIG. 13B: Representative field-of-view of fluorescently-labelled baculovirus diffusing in solution. Baculovirus was added to 0.7M $CaCl_2$ and 1 nM Atto647N-labelled DNA before being observed using a wide-field microscope. Scale bar 10 μm. Negative controls where FIG. 13C: virus, FIG. 13D: DNA or FIG. 13E: $CaCl_2$ were replaced with water were also observed. FIG. 13F: Representative tracks from the first 200 frames of the acquisition movie for fluorescently-labelled baculovirus diffusing in solution. Scale bar 10 μm. FIG. 13G: Diffusion coefficient histogram for baculovirus. n=Number of tracks.

Figure 14:
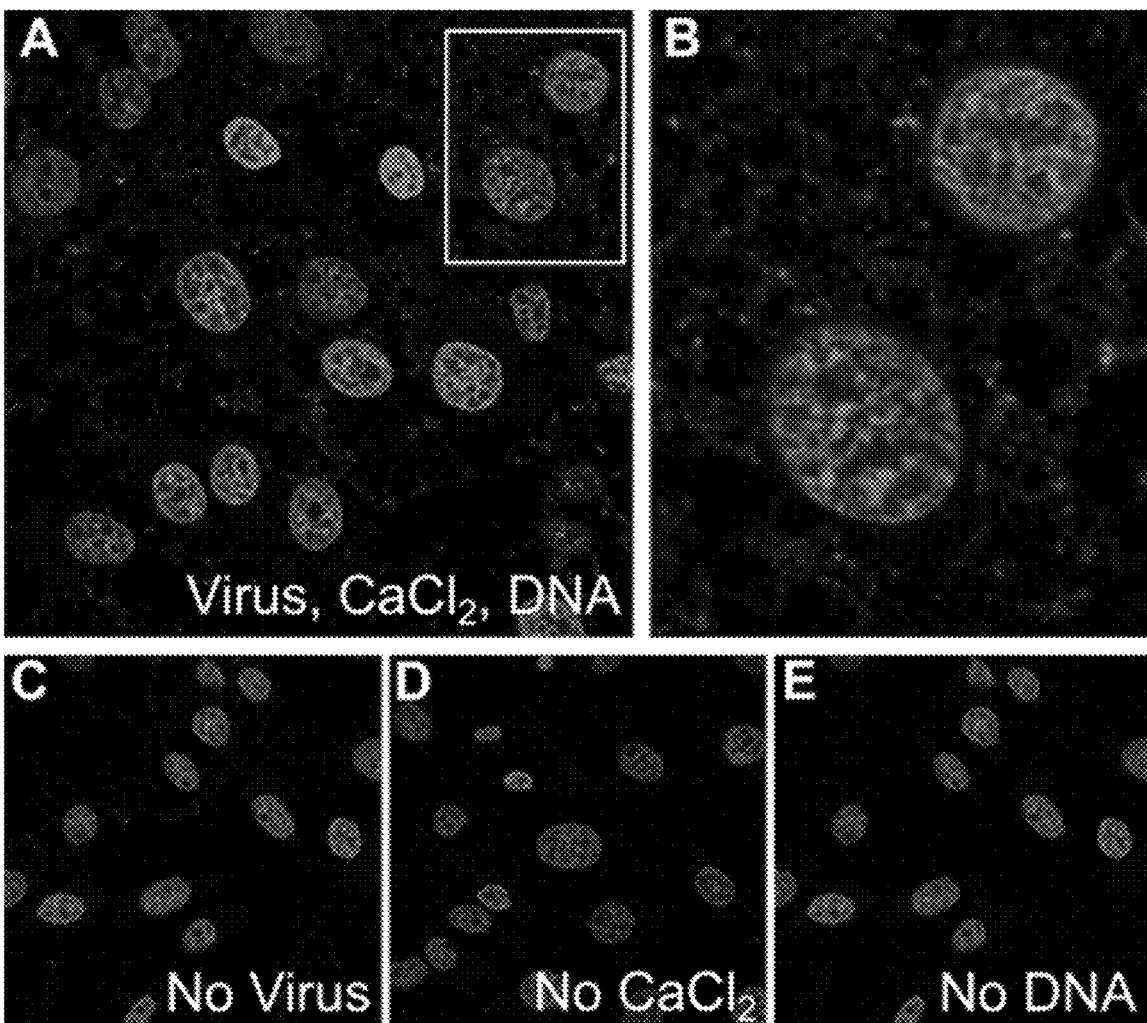

FIG. 14 shows that fluorescently-labelled influenza viruses are able to adsorb to mammalian host cells. FIG. 14A: A/Puerto Rico/8/1934 virus was added to 0.7M $CaCl_2$ and 1 nM Atto647N-labelled DNA before being used to infect MDCK cells at a multiplicity of infection of $\sim 20 \times 10^6$ PFU/mL. The cells were incubated for 1 hour at 37° C. to allow viruses to adhere before being fixed, DAPI-stained and imaged. FIG. 14B: Zoomed in image of two cells (inset from FIG. 14A). Similar experiments where FIG. 14C: virus, FIG. 14D: $CaCl_2$ or E) fluorescently-labelled DNA were substituted with water were also carried out.

Figure 15:
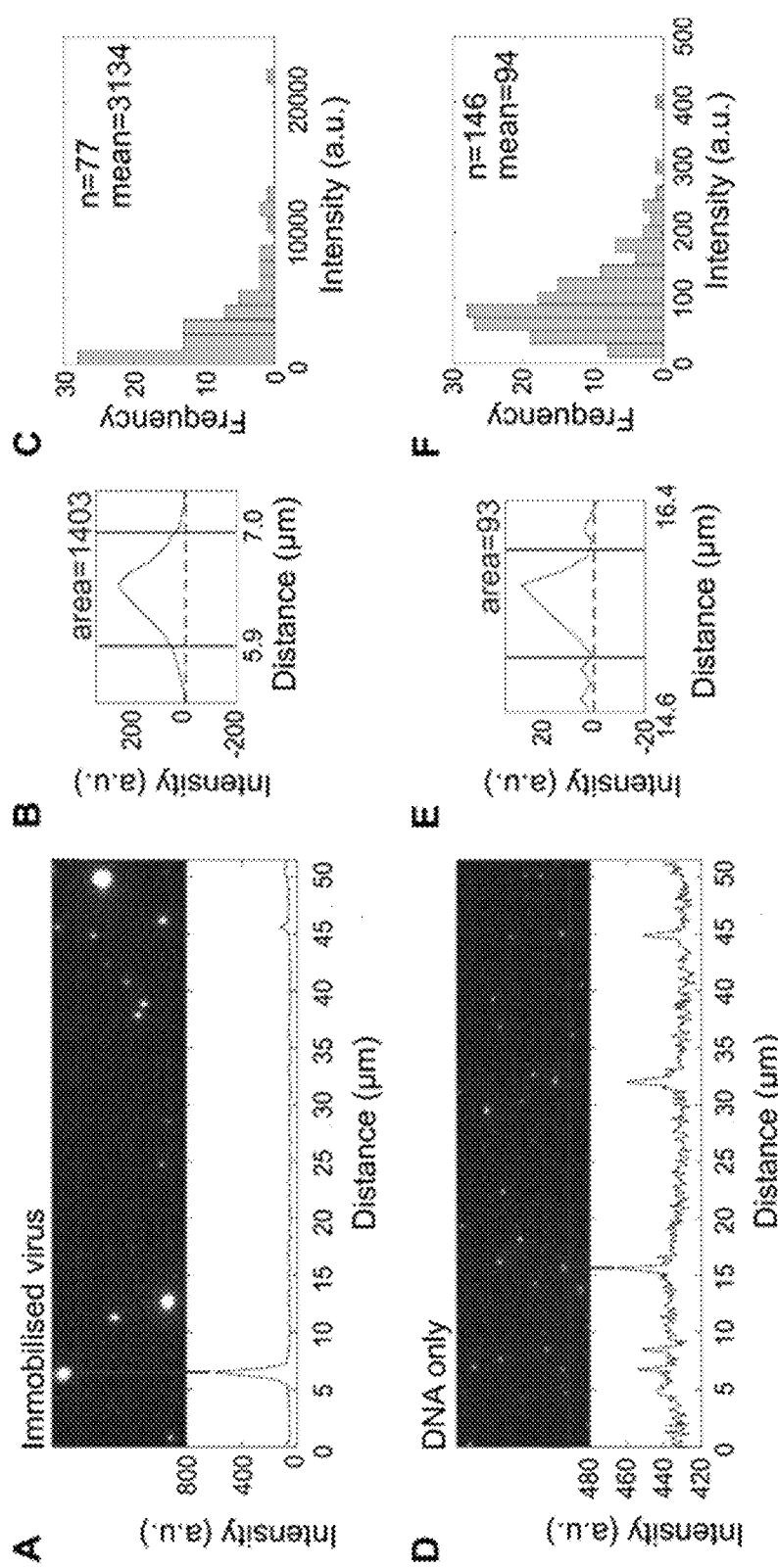

FIG. 15 shows fluorescently labelled viruses having multiple DNA molecules bound per virus particle. FIG. 15A: A/Puerto Rico/8/1934 (H1N1) virus particles were incubated with 0.65M $CaCl_2$ and 1 nM biotin-conjugated DNA labelled with Atto647N, before being immobilised on the surface of a pegylated glass slide via neutravidin. The upper panel shows a representative field-of-view of immobilised virus particles and the lower panel represents the intensity profile of the area indicated within the red box. FIG. 15B: Integration of the intensity peak corresponding to the virus particle highlighted in FIG. 15A). The dotted line indicates the local background threshold, which has been subtracted from the intensity profile, and the solid lines indicate the integration limits. FIG. 15C: Histogram of the integrated intensities of multiple virus particles. Number of virus particles (n)=77 and mean intensity 3134 a.u. FIGS. 15D-F: As for FIG. 15A-C but for DNA only. Number of virus particles (n)=146 and mean intensity 94 a.u., resulting in an average number of 3134/94=33 DNA molecules per virus particle.

Figure 16:
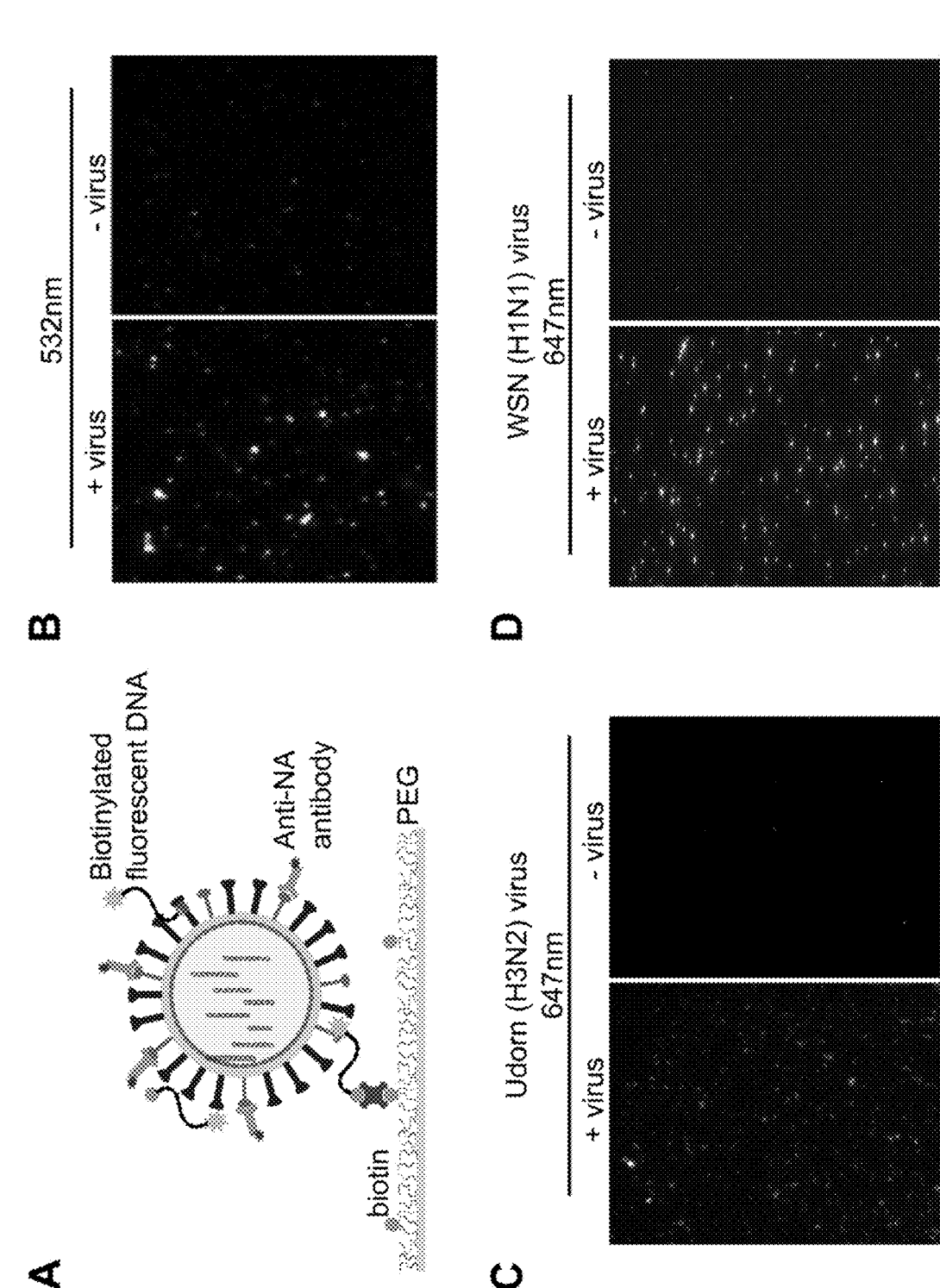

FIG. 16 shows specific antibody labelling of influenza viruses. FIG. 16A: Schematic representation of the assay; where fluorescently labelled (green fluorophore), biotinylated DNAs were used to non-specifically label and pull-down virus particles onto the surface of a glass slide. A/WSN/33 virus (WSN) at a final concentration of $49.5 \times 10^6$ PFU/mL was added to 0.65M $CaCl_2$ and 1 nM Cy3B-labelled DNA before being incubated on a pegylated (PEG) slide for 10 minutes. The slide was then washed with 1M $CaCl_2$ before being observed using a wide-field microscope. FIG. 16B: Representative field-of-view of immobilised virus particles (left panel), or a negative control lacking virus (right panel), on the surface of a glass slide, detected using a green laser (532 nm). FIG. 16C: Representative field-of-view of immobilized A/Udorn/72 (H3N2) virus particles (left panel), or a negative control lacking virus (right panel), stained with a fluorescent antibody (red fluorophore) specific to the A/Udorn/72 virus strain, detected using a red laser (647 nm). FIG. 16D: Representative field-of-view of immobilized A/WSN/33 (H1N1) virus particles (left panel), or a negative control lacking virus (right panel), stained with a fluorescent antibody (red fluorophore) specific to the A/WSN/33 virus strain, detected using a red laser (647 nm).

Figure 17:
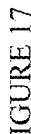

FIG. 17 shows calcium labelling of purified exosomes. Top panels: Representative fields-of-view (visualized in the green channel; 532 nm) of fluorescently labelled exosomes immobilized on a glass slide. Exosomes were double-labelled with 0.65M $CaCl_2$, 1 nM Cy3B-labelled DNA (green channel; 532 nm) and 1 nM Atto647N-labelled DNA (red channel; 640 nm) and observed using a wide-field microscope. Scale bar 10 μm. Bottom panels: Merged localisations (overlaid signals from both the red and green channels). Co-localised signals representing double-labelled exosomes are shown in yellow, and white circles represent examples of co-localised particles. Results are described in the example.

Figure 18:
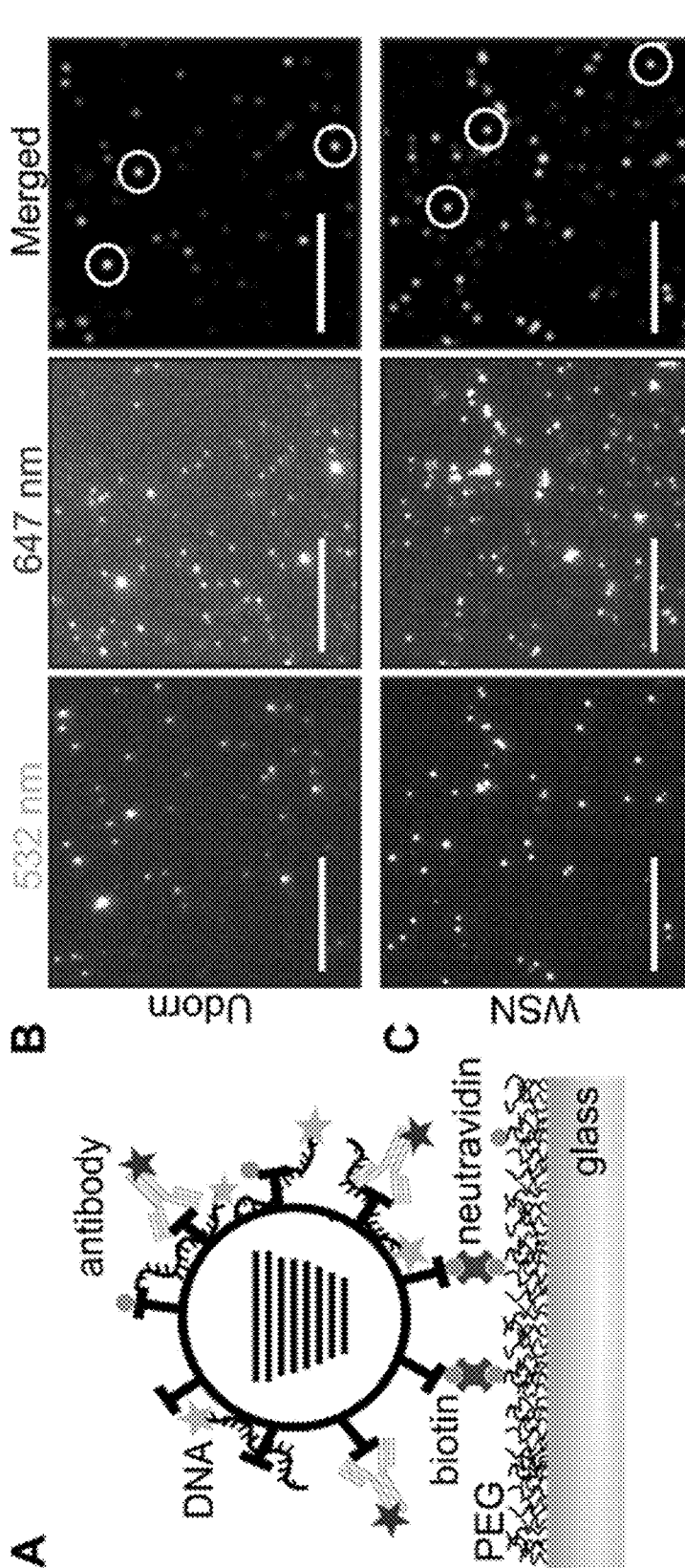

FIG. 18 shows calcium labelling of influenza viruses combined with specific antibody labelling. FIG. 18A: Schematic representation of the assay. FIG. 18B: Representative field-of-view of A/Udorn/72 (H3N2) (Udorn) virus particles; calcium-labelling detected using a green 532 nm laser (left panel), antibody-staining detected using a red 647 nm laser (middle panel) and merged red and green localisations shown in the right panel; observed on a wide-field microscope. White circles represent examples of merged localisations. Scale bar 10 μm. FIG. 18C: As B), but with $41.2 \times 10^6$ PFU/mL A/WSN/33 (H1N1) (WSN) virus particles. Results are described in the example.

DETAILED DESCRIPTION OF THE INVENTION

As explained above, the invention provides a method for functionalizing a particle with a negatively charged polymer; the particle having a negatively charged surface and a lipid coating; wherein the method comprises contacting said particle with (i) a polyvalent cation and (ii) said polymer; such that the polymer binds to the particle thereby functionalizing the particle.

As used herein, the term "functionalizing" refers to modifying the surface of a particle with a polymer as defined herein. Such functionalization can also be referred to as "labelling" the particle with the polymer. Those skilled in the art will appreciate that by functionalizing a particle with a polymer, the chemistry of the surface of the particle is typically altered according to the properties of the polymer that is used to functionalize the particle.

Typically, in the invention, the term "particle" as used herein refers to a nanoparticle. Typically the particle is a nanoparticle. Typically, the particle has an average particle size of from about 1 nm to about 5,000 nm, such as from about 10 nm to about 2,000 nm, more often from about 20 nm to about 1000 nm, such as from about 40 nm to about 900 nm e.g. from about 60 nm to about 800 nm; often from about 100 nm to about 700 nm such as from about 200 nm to about 600 nm, e.g. from about 300 nm to about 400 nm. Particle size can be measured by any suitable technique as known in the art. For example, particle size can be determined by dynamic light scattering. As used herein, the term "particle size" typically refers to the average (e.g. mean) particle size. Typically, the term "particle size" refers to a D50 particle size; more often the term "particle size" refers to a D80 particle size; usually the term "particle size" refers to a D90 particle size. As those skilled in the art will recognize, the term "D50" defines the size at which 50% of particles in a sample are smaller than the value, and 50% of particles in a sample are larger than the value. Similarly, the term "D80" defines the size at which 80% of particles in a sample are smaller than the value, and 20% of particles in a sample are larger than the value. The term "D90" defines the size at which 90% of particles in a sample are smaller than the value, and 10% of particles in a sample are larger than the value.

Any suitable particle can be used in the invention. For example, the particle is often a lipid vesicle, such as a naturally occurring vesicle (e.g. an exosome) or a synthetic liposome. A synthetic liposome is often a unilamellar liposome vesicle or a multilamellar liposome vesicle. Naturally occurring lipid vesicles can be isolated from their host organism e.g. from bacteria using methods known in the art. For example, exosomes can be purified from human or animal cells (e.g. keratinocyte cells) using commercially available kits (e.g. ExoQuick kit, System Biosciences, USA). Synthetic vesicles can be readily produced e.g. by extrusion or sonication of the appropriate lipid in aqueous solution. The formation of lipid vesicles is described in the Example.

The particle is sometimes a synthetic nanoparticle, e.g. a metal or metal-containing nanoparticle. Metal-containing nanoparticles are commercially available from suppliers such as Sigma Aldrich. Commercially available nanoparticles include gold nanoparticles (including functionalized gold nanoparticles); silver nanoparticles (including functionalized silver nanoparticles); iron oxide nanoparticles; carbon nanoparticles and the like. Any suitable nanoparticle can be used in the invention providing it has a negatively charged surface. The negatively charged surface can extend over the whole or only part of the particle. For example, the particle may have a surface having a portion that is negatively charged and a portion that is positively charged or is neutral. The particle may have a surface that is entirely negatively charged. The charge on the surface of the particle may be altered by modifying the surface of the particle. For example, a gold nanoparticle can be modified to have a negatively charged surface by coating the particle with a hydrocarbyl thiol monolayer wherein the hydrocarbyl portion of the thiol has a negative charge. A lipid coating can be used to functionalise the surface of the particle. For example, a lipid coating may comprise lipids having a negatively-charged (anionic) group. In this way, lipids in the lipid coating may provide the negatively-charged surface. A negatively charged surface can be provided for example by using a mixture of 1,2-dioleoyl-sn-glycero-3-phosphocholine (DOPC) and 1-palmitoyl-2-oleoyl-sn-glycero-3-phosphate (POPA); e.g. 3:1 DOPC:POPA.

The particle may be a naturally occurring particle e.g. a cell (e.g. a plant cell, a fungal cell, a yeast cell, an animal cell (e.g. a mammalian cell), an insect cell, or a bacterial cell) or a virus particle. However in some embodiments of the invention the particle is not a cell. Preferably the particle is not a bacterial cell or a bacterium. The particle is often a virus particle—also known as a virion—as described in more detail herein. Those skilled in the art will recognize that the invention is also applicable to damaged, partially destroyed, defective or inactivated particles such as virus particles. The invention does not depend on any particular function of the particles addressed thereby.

Typically, the particle is an enveloped virus particle. As used herein, an enveloped virus is a virus which has a coating or "viral envelope" covering their capsid. Viral envelopes are often derived from portions of the host cell membranes (phospholipids and proteins), and may also include glycoproteins. Most often an enveloped virus particle will have a lipid or lipid-containing envelope.

Any enveloped virus particle can be used in the invention. Often, the virus is a pathogenic virus. The pathogenic virus may infect plants, mammals, birds and/or fish. Typically, when the virus is a plant pathogen the virus affects a crop, for example a cereal crop, a fruit crop and/or a vegetable crop. Typically, when the virus is an avian pathogen it affects chickens, geese, turkeys and/or ducks. Typically, when the virus is a piscine pathogen affects fish it affects farmed fish such as carp, tilapia, salmon, and/or catfish. Typically, when the virus is a mammalian pathogen it affects primates, such as marmosets or monkeys, commercially farmed animals, such as horses, cows, sheep or pigs, and pets, such as dogs, cats, mice, rats, guinea pigs, ferrets, gerbils or hamsters, or humans. Most often the virus affects humans i.e. it is a human pathogen.

The particle may also be a bacteriophage (phage). Bacteriophages typically affect bacteria and/or archaea. As used herein, the term "virus" includes bacteriophages. Typically, in the invention, a bacteriophage has a lipid component such as a lipid membrane and/or a lipid envelope.

Typically, in the invention, the particle is a virus particle wherein the virus is an enveloped virus selected from herpesviridae, poxviridae, pneumoviridae, hepadnaviridae, flaviviridae, togaviridae, coronaviridae, hepatitis D virus, orthomyxoviridae, paramyxoviridae, rhabdoviridae, bunyaviridae, filoviridae, baculoviridae and retroviridae. Most often the virus is an influenza virus, for example the virus may be an influenza A, influenza B, influenza C or influenza D virus. Most often the virus is an influenza A virus. The virus may be an avian influenza virus. The virus may be a porcine influenza virus. Often, the virus is a zoonotic virus. Sometimes, the virus is an epidemic or pandemic influenza virus. The influenza virus may for example be selected from H1N1, H2N2, H3N2, H5N1, or H7N9.

Typically, in the invention, the virus is present in a biological fluid. The virus may be present in any suitable biological fluid. For example, the virus may be present in blood, plasma, serum, urine, lymph, saliva, mucus, amniotic, or allantoic fluid. The virus may be obtained from a nasal swab, a sputum sample, or lung fluid. Often, in the invention, the biological fluid is a sample obtained from a subject infected with a viral infection. In other embodiments the biological fluid is a fluid used to deliberately culture viral proliferation e.g. for vaccine production, such as a cell culture medium or allantoic fluid. It will be apparent that the method of the invention is typically carried out in vitro.

In the invention, any suitable polyvalent cation can be used. For example, the cation can be a metal cation (such as a polyvalent metal cation) or an organic cation (e.g. a polyamine e.g. spermine). Usually, the polyvalent cation is a polyvalent metal cation. A polyvalent metal cation is typically a divalent, trivalent or tetravalent metal cation. More typically the cation is a divalent or trivalent metal cation. Most often the cation is a divalent metal cation.

Any suitable metal cation can be used. Divalent metal cations include for example cations of magnesium, calcium, strontium, vanadium, chromium, manganese, iron, cobalt, nickel, copper and zinc. Calcium ($Ca^{2+}$) is most often used in the invention.

Divalent calcium ($Ca^{2+}$) can be provided in any suitable form. For example, the Ca2+ can be provided as $CaBr_2$, $CaCO_3$, $CaCl_2$, CaNCN, $CaF_2$, $CaH_2$, $Ca(OH)_2$, $Ca(IO_3)_2$, $CaI_2$ (including hydrates thereof, $CaI_2 \cdot xH_2O$); $Ca(NO_2)_2$ (including hydrates thereof, $Ca(NO_3)_2 \cdot xH_2O$); $CaC_2O_4$ (including hydrates thereof, $CaC_2O_4 \cdot xH_2O$), $Ca(ClO_4)_2$ (including hydrates thereof, e.g. $Ca(ClO_4)_2 \cdot xH_2O$), $Ca(H_2PO_4)_2$, $[Ca_5(OH)(PO_4)_3]_x$, $Ca_2P_2O_7$, $CaSO_4$, and $Ca(SCN)_2$ (including hydrates thereof, $Ca(SCN)_2 \cdot xH_2O$). More usually $Ca^{2+}$ is provided as $CaBr_2$, $CaCO_3$, $CaCl_2$, $CaF_2$, $Ca(OH)_2$, $CaI_2$, or $CaSO_4$, or $Ca(NO_2)_2$. Most often in the invention, the $Ca^{2+}$ is provided as $CaCl_2$.

The polyvalent cation (e.g. divalent calcium) can be provided in any suitable state. As will be apparent from the discussion of the invention herein, typically, in the invention, the polyvalent cation (e.g. divalent calcium) is provided in the form of a solution with a suitable solvent. Typically the polyvalent cation (e.g. divalent calcium) is not provided as a solid. Typically, in the invention, the polyvalent cation (e.g. divalent calcium) does not precipitate when contacted with the particle; e.g. the polyvalent cation (e.g. divalent calcium) typically does not precipitate on the surface of the particle.

In embodiments of the invention wherein the polyvalent cation is provided as a solution, any suitable solvent can be used. For example, the solvent may be an organic solvent, an aqueous solvent, or an ionic liquid. Suitable organic solvents include alcohols (e.g. methanol, ethanol, isopropanol, etc) and carboxylic acids (e.g. acetic acid, benzoic acid, etc). Most commonly the solvent is an aqueous solvent, e.g. water, which may further comprise one or more additional components e.g. buffering agents. Buffering agents include agents such as MES (2-(N-morpholino)ethanesulfonic acid), PIPES (Piperazine-N,N'-bis(2-ethanesulfonic acid)), MOPS (3-(N-morpholino)propanesulfonic acid), TES (2-[[1,3-di-hydroxy-2-(hydroxymethyl)propan-2-yl]amino]ethane-sulfonic acid), HEPES (4-(2-hydroxyethyl)-1-pipera-zineethanesulfonic acid), TAPSO (3-[N-Tris (hydroxymethyl)methylamino]-2-hydroxypropanesulfonic acid), Tricine (3-[N-Tris(hydroxymethyl)methylamino]-2-hydroxypropanesulfonic acid), Tris (Tris(hydroxymethyl) aminomethane) or, (2-Amino-2-(hydroxymethyl)propane-1, 3-diol), phosphate (e.g. sodium or potassium phosphate monobasic/dibasic); citric acid —$Na_2HPO_4$, citric acid/cit-rate (e.g. citric acid-sodium citrate), acetate/acetic acid (e.g sodium, acetate-acetic acid), imidazole, carbonate/bicarbon-ate (e.g. sodium carbonate-sodium bicarbonate), etc.

The term "negatively charged polymer" as used herein refers to a polymer having a negatively charged portion. For example, the negative charge can extend over the whole or only part of the polymer. For example, the polymer may have a portion that is negatively charged and a portion that is positively charged or is neutral. The polymer may be substantially negatively charged e.g. a polynucleotide, such as a polynucleotide comprising 5 or more nucleotides.

Typically, in the invention, the negatively charged polymer is a polynucleotide, a polypeptide, a polysaccharide or a negatively charged polyether. Sometimes, the negatively charged polymer is a polynucleotide, a polysaccharide or a negatively charged polyether. More often, the negatively charged polymer is a polynucleotide, a polypeptide, or a polysaccharide. Still more often, the negatively charged polymer is a polynucleotide or a polypeptide. In some embodiments the negatively charged polymer is not a polypeptide. Sometimes, the negatively charged polymer is an oligopeptide but not a protein. Sometimes, the negatively charged polymer is not a protein. Typically, the negatively charged polymer does not comprise a binding site for ligands on the particle surface. For example, in embodiments wherein the particle comprises groups such as carbohydrate groups on the particle surface, the negatively charged polymer may not comprise receptor binding sites for such groups (e.g. carbohydrate recognition domains). Most often the negatively charged polymer is a polynucleotide.

The negatively charged polymer may be a polynucleotide, i.e. a nucleic acid sequence. Nucleic acids are negatively charged. A nucleic acid is a macromolecule comprising two or more nucleotides. The nucleotides can be naturally occurring or artificial. A nucleotide typically contains a nucleobase, a sugar and at least one phosphate group. The nucleobase is typically heterocyclic. Nucleobases include, but are not limited to, purines and pyrimidines and more specifically adenine, guanine, thymine, uracil and cytosine. The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide. Suitable nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The nucleotides are usually selected from AMP, TMP, GMP, UMP, dAMP, dTMP, dGMP or dCMP.

When the negatively charged polymer is a polynucleotide, the polynucleotide may be single or double stranded. Usually, when the negatively charged polymer is a polynucleotide, the polynucleotide is single stranded, such as cDNA or RNA. Often, when the negatively charged polymer is a polynucleotide, the polynucleotide is a long double- or single-stranded polynucleotide. Typically, a long double-stranded polynucleotide is used, for example the negatively charged polymer is often a plasmid or is selected from extracted phage DNA, such as λ or M13 DNA. A long double-stranded polynucleotide often has a length of from about 5,000 base pairs (bp) (i.e. about 5 Kbp) to about 5 Mbp, e.g. from about 5 Kbp to about 50 Kbp. In other embodiments of the invention, the negatively charged polymer is a shorter polynucleotide e.g. having from about 2 to about 5,000 nucleotides. For example, when the negatively charged polymer is a single stranded polynucleotide, the polynucleotide may comprise from about 2 to about 1000 nucleotides, such as from about 5 to about 500 nucleotides, e.g. from about 10 to about 100 nucleotides, such as from about 20 to about 80 nucleotides e.g. from about 30 to about 70 nucleotides. When the negatively charged polymer is a double stranded polynucleotide, each strand of the double stranded polynucleotide may independently comprise from about 2 to about 1000 nucleotides, such as from about 5 to about 500 nucleotides, e.g. from about 10 to about 80 nucleotides, such as from about 20 to about 80 nucleotides e.g. from about 30 to about 70 nucleotides. The negatively charged polymer may be an oligonucleotide. As used herein an oligonucleotide is typically a short polynucleotide having e.g. between 2 and 100 nucleotides, e.g. from about 20 to about 80 nucleotides e.g. from about 30 to about 70 nucleotides.

The negatively charged polymer may be a polypeptide. The polypeptide may be e.g. a fragment of a protein. The polypeptide can be naturally-occurring or non-naturally-occurring. The polypeptide can include within it synthetic or modified amino acids. The polypeptide can be one that is secreted from cells. Alternatively, the polypeptide can be one that is present inside cells such that it must be extracted from the cells before the invention can be carried out. It can be extracted both by the use of antibodies or by the binding of an affinity tag introduced on the protein. The polypeptide is more often synthetically produced e.g. by solid-phase peptide synthesis. When the negatively charged polymer is a polypeptide, it is often a polymer of from about 2 to about 1000 amino acids, such as from about 5 to about 500 amino acids, e.g. from about 10 to about 100 amino acids, such as from about 20 to about 80 amino acids e.g. from about 30 to about 70 amino acids. A polypeptide of less than about 100 amino acids is also referred to as an oligopeptide.

The negatively charged polymer may be a polysaccharide. A polysaccharide is a polymeric carbohydrate molecule composed of chains of monosaccharide units bound together by glycosidic linkages. A polysaccharide may be linear or branched. A polysaccharide may be homogeneous (comprising only one repeating unit) or heterogeneous (containing modifications of the repeating unit). Polysaccharides include callose or laminarin, chrysolaminarin, xylan, arabinoxylan, mannan, fucoidan and galactomannan. When the negatively charged polymer is a polysaccharide, the polysaccharide may comprise from about 2 to about 1000 monosaccharide units, such as from about 5 to about 500 monosaccharide units, e.g. from about 10 to about 100 monosaccharide units, such as from about 20 to about 80 monosaccharide units e.g. from about 30 to about 70 monosaccharide units.

The negatively charged polymer may be a polyether e.g. a polyethylene glycol. When the negatively charged polymer is a polyether the polyether may be modified. Any suitable modification can be made. A negatively charged polyether can be linear or branched. When the negatively charged polymer is a polyether, the polyether may comprise from about 2 to about 1000 ethylene glycol units (or modified derivatives thereof), such as from about 5 to about 500 units, e.g. from about 10 to about 100 units, such as from about 20 to about 80 units e.g. from about 30 to about 70 units.

The negatively charged polymer may consist of or comprise a synthetic peptide nucleic acid polymer, such as a peptide nucleic acid (PNA). For example, a double-stranded DNA-PNA hybrid polymer may be used. A polymeric PNA consists of repeating PNA units each of which typically comprises a nucleobase linked to a peptide backbone; for example PNA may comprise a backbone comprising repeating N-(2-aminoethyl)-glycine units linked by peptide bonds, with nucleobases (e.g. purine and/or pyrimidine bases) linked to the backbone by alkylcarbonyl (e.g. —C(O)—CH$_2$—) linkers. When the negatively charged polymer consists of or comprises PNA, the PNA typically comprises from about 2 to about 1000 PNA units, such as from about 5 to about 500 units, e.g. from about 10 to about 100 units, such as from about 20 to about 80 units e.g. from about 30 to about 70 units. When the PNA is present in a DNA-PNA hybrid polymer, the hybrid polymer typically comprises from about 2 to about 1000 DNA nucleotides, such as from about 5 to about 500 nucleotides, e.g. from about 10 to about 100 nucleotides, such as from about 20 to about 80 nucleotides e.g. from about 30 to about 70 nucleotides and from about 2 to about 1000 PNA units, such as from about 5 to about 500 units, e.g. from about 10 to about 100 units, such as from about 20 to about 80 units e.g. from about 30 to about 70 PNA units.

In the invention, the negatively charged polymer typically comprises a detectable label and/or an immobilisation tag and/or one or more reactive functional groups. Typical detectable labels include optically detectable labels. Often, a detectable label is an optically detectable label such as a fluorescent or chemiluminescent label. Any suitable fluorescent or chemiluminescent label can be used. For example, the fluorescent or chemiluminescent label may be a dye.

When the negatively charged polymer is a polynucleotide, a fluorescent or chemiluminescent label may be incorporated at the 5' and/or 3' end of the polynucleotide; and/or may be at an intervening location in the polynucleotide. The fluorescent or chemiluminescent label may be a commercially available dye. Polynucleotides modified with suitable fluorescent or chemiluminescent labels are commercially available from suppliers such as IDT Technologies (UK) or IBA (Germany).

When the negatively charged polymer is a polynucleotide, the fluorescent or chemiluminescent label may be selected from, for example, 6-FAM (NHS Ester), 6-FAM (Fluorescein), Fluorescein dT, Cy3, Cy3B, TAMRA, JOE (NHS Ester), Cy5, TAMRA (NHS Ester), MAX (NHS Ester), TET, Cy5.5, ROX (NHS Ester), TYE 563, Yakima Yellow, HEX, TEX 615, TYE 665, TYE 705; Alexa Fluor Dyes such as Alexa Fluor 488, 532, 546, 594, 647, 660 and 750 (NHS Esters); LI-COR IRDyes such as 5' IRDye 700, 800 and 800CW (NHS Esters); ATTO Dyes such as ATTO 488, 532, 550, 565, Rho101, 590, 633 and 647N (NHS Esters); Rhodamine Dyes such as Rhodamine Green-X, Rhodamine Red-X (NHS Esters), 5-TAMRA (Azide); WellRED Dyes such as WellRED D4, D3 and D2 Dyes; 6-FAM (Azide), Texas Red-X (NHS Ester), Lightcycler 640 (NHS Ester), and Dy 750 (NHS Ester). Most often the dye is selected from ATTO647N, Cy3B and Cy3.

When the negatively charged polymer comprises an immobilization tag, any suitable immobilization tag can be used. For example, the immobilization tag may be an affinity tag. Examples include peptide tags such as calmodulin tags (typically KRRWKKNFIAVSAANRFKKISSSGAL; SEQ ID NO:1), polyglutamate tags, E-tags (typically GAPVPYPDPLEPR; SEQ ID NO:2); FLAG-tags (typically DYKDDDDK; SEQ ID NO:3); HA-tags (typically YPYDVPDYA; SEQ ID NO:4); polyhistidine tags, Myc-tags (typically EQKLISEEDL; SEQ ID NO:5), an NE-tag (typically TKENPRSNQEESYDDNES; SEQ ID NO:6), an S-tag (typically KETAAAKFERQHMDS; SEQ ID NO:7), an SBP-tag (typically MDEKTTGWRGGHVVEG-LAGELEQLRARLEHHPQGQREP; SEQ ID NO:8); a Spot-tag (typically PDRVRAVSHWSS, SEQ ID NO:9), a Strep-tag (typically WSHPQFEK; SEQ ID NO:10), a TC tag (typically CCPGCC; SEQ ID NO:11), a Ty tag (typically EVHTNQDPLD; SEQ ID NO:12), a V5 tag (typically GKPIPNPLLGLDST; SEQ ID NO:13), a VSV-tag (typically YTDIEMNRLGK; SEQ ID NO:14), an Xpress tag (typically DLYDDDDK; SEQ ID NO:15), an Isopeptag (typically TDKDMTITFTNKKDAE; SEQ ID NO:16), a SpyTag (typically AHIVMVDAYKPTK; SEQ ID NO:17), a SnoopTag (typically KLGDIEFIKVNK; SEQ ID NO:18), and the like. Other examples include chemical tags such as biotin tags. Typically, in the invention, when an affinity tag is present it is a biotin tag.

Typically, in the invention, the negatively charged polymer is not encapsulated by a virus prior to being bound to the particle. For example, it is known that DNA can be enveloped by viral particles and precipitated on the surface of cells wherein the viral particles are takin into the cell by endocytosis. Those skilled in the art will appreciate that such methods are very different to those of the invention wherein the negatively charged polymer binds to the particle as described herein. Thus, the invention typically does not comprise binding a negatively charged polymer to a particle (e.g. a cell) by encapsulating the negatively charged polymer within an enveloped virus particle.

As explained above, in the invention the polymer binds to the particle thereby functionalizing the particle. As those skilled in the art will appreciate, the binding between the particle and the polymer can be stable or even transient. Without being bound by theory, the inventors believe that the duration and stability of the binding can be controlled by controlling the length of the polymer used in the method. The binding is typically not a covalent bonding but is more often an ionic interaction between the charged particle, the charged polymer and the charged cation.

Thus, in the invention, the binding between the negatively charged polymer and the particle typically comprises binding between the negatively charged polymer and the lipid coating of the particle. For example, the binding may comprise binding between the negatively charged polymer and negatively charged groups (e.g. negatively charged head groups) of the lipid coating of the particle. Said binding may thus be mediated by the polyvalent cation. Typically, therefore, in the methods of the invention, the binding comprises binding between negatively-charged groups of lipids in the lipid coating, the polyvalent cation, and the negatively-charged polymer. For instance, negatively charged groups of the polymer and the negatively charged groups of the lipids may form a coordination complex with the polyvalent cation. Without being bound by theory, such binding is believed to consist of or comprise an ionic or predominantly ionic interaction between negatively charged groups on the negatively charged polymer, the polyvalent cation and negatively charged groups on the lipid coating of the particle. In other words, in the methods of the invention, the binding typically comprises an ionic or predominantly ionic interaction between negatively charged groups of lipids in the lipid coating, the polyvalent cation, and the negatively charged polymer.

In some embodiments, such charge-mediated binding may be described as non-specific binding. Those skilled in the art will appreciate that as used herein, "non-specific binding" refers to the charge mediated binding described herein. Such non-specific binding may thus exclude, for example, the specific binding of ligands on a particle surface (e.g. carbohydrate groups) to ligand binding sites (e.g. receptors) on a negatively charged polymer such as a protein (e.g. carbohydrate binding sites, e.g. carbohydrate recognition domains). The term "non-specific" binding does not imply that there is no specific binding of the polyvalent cation to the particle and/or the negatively charged polymer; rather the term implies that the binding is directed primarily by charge interactions between the negatively charged polymer, the polyvalent cation and negatively charged groups on the lipid coating of the particle rather than being determined by the specific interaction between ligands on the particle and ligand binding sites on the polymer.

The methods of the invention are typically carried out in solution. Typically aqueous solutions are used. For example, the solution is often a buffered salt solution having a pH of between about 4 and about 9, more often between about 5.5 and about 8. The methods can be typically carried out in very small solution volumes or in larger volumes depending on the application of the methods intended. Often, the solution volume is from about 10 μL to about 1000 μL, often from about 10 μL to about 100 μL e.g. from about 20 μL to about 50 μL.

The conditions used in the method are typically controlled in order to yield desired results. For example, the method is typically amenable to functionalising from about $10^1$ particles/mL of reaction solution. More often, the concentration of particles used in the method of the invention is at least about $10^2$ particles/mL, such as at least about $10^3$ particles/mL, e.g. at least about $10^4$ particles/mL such as at least about $10^5$ particles/mL, typically at least $10^6$ particles/mL. There is no particular upper limit on the concentration of particles used in the method of the invention, but often the concentration of particles used in the method of the invention is no more than about $10^{10}$ particles/mL, such as less than $10^9$ particles/mL e.g. less than $10^8$ particles/mL such as less than $10^7$ particles/mL.

In the invention, when the particle is a virus particle the concentration of virus particles used in the methods of the invention is typically at least about $10^1$ plaque-forming units (PFU)/mL of reaction solution. More often, the concentration of virus particles used in the method of the invention is at least about $10^2$ PFU/mL, such as at least about $10^3$ PFU/mL, e.g. at least about $10^4$ PFU/mL such as at least about $10^5$ PFU/mL, typically at least $10^6$ PFU/mL. There is no particular upper limit on the concentration of virus particles used in the method of the invention, but often the concentration of virus particles used in the method of the invention is no more than about $10^{10}$ PFU/mL, such as less than $10^9$ PFU/mL e.g. less than $10^8$ PFU/mL such as less than $10^7$ PFU/mL.

The concentration of polyvalent cation used in the methods of the invention is typically from about 1 mM to about 2 M, such as from about 10 mM to about 1 M, e.g. from about 20 mM to about 500 mM such as from about 40 mM to about 400 mM e.g. from about 50 mM to about 300 mM such as from 60 mM to about 200 mM e.g. from about 65 mM to about 100 mM.

The concentration of negatively charged polymer used in the methods of the invention is typically from about 0.01 nM to about 100 nM, e.g. from about 0.1 nM to about 10 nM such as from about 0.5 nM to about 5 nM, e.g from about 0.7 nM to about 1.5 nM, often about 1 nM.

For example, in embodiments of the invention wherein the particle is an enveloped virus particle; the polyvalent cation is $Ca^{2+}$ and the negatively charged polymer is a polynucleotide; the method typically involves contacting in solution at least about $10^2$ PFU/mL viral particles with at least about 10 mM $Ca^{2+}$ and at least about 1 nM polynucleotide.

The methods of the invention are very rapid—this is a particular advantage of the invention compared to previously known methods. Whilst the methods are amenable to operating over prolonged timescales, more typically the methods of the invention comprise contacting the particle with the polyvalent cation and the negatively charged polymer for less than about 30 minutes, such as for less than about 20 minutes, e.g. for less than about 15 minutes, such as for less than about 10 minutes, often for less than about 5 minutes, e.g. for less than about 4 minutes, often less than about 3 minutes, such as less than 2 minutes, e.g. less than 1 minute.

Surprisingly, the inventors have found that viral particles functionalized in accordance with the invention retain their ability to bind to host cells. This surprising finding indicates that viral particles functionalized in accordance with the invention maintain their structural integrity. It further suggests that haemagglutinin proteins typically expressed on the surface of viral particles remain available for binding to host cell receptors even after functionalization. It could not be predicted that viral particles functionalized in accordance with the invention would retain this activity. Accordingly, when the particle used in the method of the invention is an enveloped virus particle, the method often further comprises the step of binding the functionalized virus particle to a host cell.

The inventors have further found that the binding of the negatively charged polymer to the particle can be reversed by contacting the functionalised particle obtained in the methods of the invention with a chelating agent for the polyvalent cation. Any suitable chelating agent can be used depending on the polyvalent cation employed in the invention. Chelating agents include ethylene diamine, vitamin B-12, EDTA, and the like. EDTA is particularly often used in the methods of the invention.

The inventors have shown that the method of the invention can advantageously be combined with strain-specific detection assays. In particular, the inventors have successfully managed to pull down viruses using the method of the invention, and image them in one colour, and then use a strain-specific antibody to label immobilized viruses, imaged in a second colour (see FIG. 16 and the corresponding section of the Examples herein).

Accordingly, in one embodiment of the method of the invention as defined herein, the particle is an enveloped virus particle and the virus is of a particular type, and the method further comprises identifying the enveloped virus particle as being a virus of that particular type. The step of identifying the enveloped virus particle as being a virus of that particular type may be any known method for identifying a virus of the particular type. It is typically an assay method for detecting a virus of the particular type. The particular "type" of virus may be a particular order, family, subfamily, genus, species, or strain of virus. It may be any of the specific types of viruses listed herein. Often, the particular type of virus is a particular strain of virus. The assay method for detecting a virus of the particular type may for instance be a strain-specific detection assay. The assay may for instance comprise antibody, aptamer or complementary genome probe labelling.

Usually, when the method of the invention further comprises identifying the enveloped virus particle as being a virus of a particular type, the negatively charged polymer comprises an immobilisation tag and/or a first detectable label. Usually, the negatively charged polymer comprises an immobilisation tag and, optionally, a first detectable label. The first detectable label may for instance be an optically detectable label, for instance a fluorescent or chemiluminescent label. Thus, often, the method of the invention comprises: contacting the immobilisation tag with a substrate therefor, such that the immobilisation tag binds to the substrate and thereby immobilises the enveloped viral particle on the substrate, optionally detecting the first detectable label and thereby detecting the immobilised particle, and the method may they further comprise the step of identifying the enveloped virus particle as being a virus of a particular type.

Identifying the enveloped virus particle as being a virus of a particular type typically comprises contacting the enveloped viral particle—which is typically immobilised on a substrate as described above—with an agent for identifying viruses of a particular type. The agent may comprise an antibody specific for the virus type, for instance a strain-specific antibody. It may for instance comprise an aptamer, or a complementary genome probe, which is specific for the virus type, for instance a strain-specific aptamer or a complementary genome probe. The agent often further comprises a second detectable label. The second detectable label is generally different from the first detectable label, such that viruses of the particular type may be distinguished from the enveloped viral particles in general which are identifiable by the first detectable label. The second detectable label may for instance be an optically detectable label, for instance a fluorescent or chemiluminescent label. The fluorescence or chemiluminescence is usually different from that in the first detectable label, for instance it is typically a different colour.

Thus in one embodiment the invention provides a method of identifying a virus of a particular type, which method comprises:

a) functionalizing enveloped viral particles in a sample with a negatively charged polymer by a method as defined anywhere herein wherein the negatively charged polymer comprises an immobilisation tag and, optionally, a first detectable label;

b) contacting the immobilisation tag with a substrate therefor such that the immobilisation tag binds to the substrate and thereby immobilises the enveloped viral particles on the substrate;

c) optionally, detecting the first detectable label;

d) contacting the enveloped viral particles with an agent for identifying viruses of a particular type, optionally wherein the agent comprises a second detectable label; and e) identifying any viruses of the particular type, optionally by detecting the second detectable label. Optionally, the agent is a strain-specific agent, for instance a strain-specific antibody, aptamer or complementary genome probe.

In addition to providing methods for functionalizing particles, the invention also provides functionalized particles per se. The invention thus provides particles which are obtainable by the methods of the invention, as described herein.

The invention also provides a functionalized particle, comprising:

a particle having a negatively charged surface and a lipid coating;

a negatively charged polymer; and a polyvalent cation which binds the polymer to the particle.

Typically, the particle, the negatively charged polymer and the polyvalent cation are as described herein. The binding between the polyvalent cation, the polymer and the particle may also be as further defined anywhere herein. For instance, as discussed above in relation to the method of the invention, the binding typically comprises binding between negatively-charged groups of lipids in the lipid coating, the polyvalent cation, and the negatively-charged polymer. Thus, in the functionalized particle of the invention, the polyvalent cation may bind negatively-charged groups of lipids in the lipid coating to the negatively-charged polymer. Negatively charged groups of the polymer and the negatively charged groups of the lipids may for instance form a coordination complex with the polyvalent cation. Often, in the functionalized particle of the invention, the polyvalent cation binds negatively-charged groups of lipids in the lipid coating to the negatively-charged polymer, wherein the binding comprises an ionic or predominantly ionic interaction between the negatively charged groups of the lipids in the lipid coating, the polyvalent cation, and the negatively charged polymer.

The invention also provides compositions comprising functionalized particles obtainable by the methods of the invention, or as otherwise described herein, and a carrier medium. Any suitable carrier medium can be used in such compositions. For example, the carrier medium may be an aqueous or organic solvent, with aqueous solutions being preferred. The carrier medium may be a biological fluid as described herein, for example a cell culture medium. The carrier medium may be an analysis fluid, for example a buffered salt solution. The carrier medium typically comprises water.

The invention also provides beneficial applications for functionalized particles such as those produced as described herein.

In one embodiment, the invention provides a method of binding a functionalized virus particle to a host cell. The method comprises binding to a host cell a functionalized particle as defined herein; wherein the particle is an enveloped virus particle as defined herein. Such methods can be used in vaccine production, virus analysis, pathogenicity studies and the like.

In another embodiment, the invention provides a method of releasing a polymer from a functionalized particle. The method comprises contacting the functionalized particle with a chelating agent for the polyvalent cation. The functionalized particle and chelating agent is typically as described herein. Such methods can be used in purification processes e.g. viral purification processes, and for downstream processing of particles.

One aspect of the present invention involves the detection of functionalized particles. For example, the present inventors have found that when a particle is functionalized by binding a negatively charged polymer comprising an optically detectable label to the particle, the resultant functionalized particle can beneficially be detected by optical tracking. Protocols for optically tracking particles are described in the Example.

Thus, the invention also provides a method of optically tracking a particle having a negatively charged surface and a lipid coating. The method comprises a) functionalizing the particle with a negatively charged polymer by a method as described herein, wherein the negatively charged polymer comprises an optically detectable label; and b) optically tracking the optically detectable label thereby tracking the particle Preferably, in such methods, the particle is an enveloped viral particle as described herein.

The invention also provides methods of tracking particles produced by the methods of the invention described herein. For example, when the negatively charged polymer comprises an optically detectable label, the invention provides methods comprising optically tracking the optically detectable label. The particle and optically detectable label are typically as described herein.

The present inventors have recognised that it is often advantageous to functionalize the surface of particles with a reactive functional group. Such functionalizing can be useful to introduce reactivity to a particle for downstream applications. Thus, the invention provides a method of functionalizing the surface of a particle having a negatively charged surface and a lipid coating. The method comprises functionalizing the particle with a negatively charged polymer in a method as described herein; wherein the negatively charged polymer comprises one or more reactive functional groups; such that the polymer binds to the surface of the particle thereby functionalizing the surface of the particle. Preferably, in such methods, the particle is an enveloped viral particle as described herein.

It is typically useful to isolate particles such as enveloped viral particles from samples, for example for further analysis or downstream processing. In another embodiment, therefore, the invention provides a method of isolating enveloped viral particles from a sample, comprising:

a) functionalizing the enveloped viral particles in the sample with a negatively charged polymer as described herein; wherein the negatively charged polymer comprises an immobilization tag;

b) contacting the immobilisation tag with a substrate therefor such that the immobilisation tag binds to the substrate;

c) isolating the substrate from the sample; and d) optionally releasing the viral particles from the substrate.

Typically the immobilization tag is as described herein. Any suitable substrate can be used. For example, when the immobilization tag is a biotin tag, the substrate may be a surface such as a resin, bead, organic or inorganic surface etc functionalized with streptavidin, neutravidin, traptavidin, or any other moiety which binds to biotin. Streptavidin and neutravidin (particularly neutravidin) are typically used. Other similar techniques can be used for alternative immobilization tags. For example, if the immobilization tag is a polyhistidine tag (for example, often if the negatively charged polymer is a polypeptide) the substrate may be a metal substrate such as a cobalt or nickel substrate such that the polyhistidine tag binds to the substrate.

The method often involves isolating the substrate from the sample. Any suitable isolation technique can be used. For example, the substrate can be isolated from the sample by filtration, centrifugation, evaporation, or (when the substrate is magnetic) by magnetic attraction of the substrate and removal of the sample medium. Most often, the substrate is magnetic (e.g. in the form of magnetic beads) and the substrate is removed by magnetic attraction of the substrate in order to retain the substrate in a vessel and removal of the sample medium.

The invention is particularly useful for quantifying enveloped virus particles in a sample. Such techniques are an important aspect of vaccine production and industrial virology. Accordingly, the invention provides a method of quantifying enveloped virus particles in a sample, comprising:

a) functionalizing the enveloped viral particles in the sample with a negatively charged polymer as described herein; wherein the negatively charged polymer comprises a detectable label;

b) detecting the detectable label; and c) determining the number or concentration of detectable labels in the sample thereby quantifying the number or concentration of labelled viral particles in the sample.

The detectable label can be detected by any suitable means. For example, the detectable label is often an optically detectable label, such as a fluorescent label as described herein. The method typically involves detecting the label by passing the labelled viral particles in the sample through a fluidics system having a detection zone and comprising an optical detector, photo-illuminating the detection zone and thereby detecting fluorescence of the labelled viral particles in the detection zone. Typically, the optical detector detects the fluorescence emitted by the particles upon photoillumination and thus allows the concentration of labels, and thus the concentration of labelled (functionalized) particles in the sample to be determined.

The invention is fully compatible with methods for the specific detection of viral particles, e.g by using polymers comprising or consisting of complementary genome probes, antibodies or aptamers. Those skilled in the art will recognize that in this way the methods of the invention can be used to specifically label, detect or functionalize specific viruses in a sample.

As described in more detail herein, optical tracking is often used in the methods of the invention to detect and monitor the functionalized particles. The optical tracking techniques can yield detailed information about the functionalized particles thereby tracked. For example, optical tracking allows the average diffusion coefficient for the functionalized particles to be determined, which in turn yields information regarding their average size, etc. When the particles thus probed are viral particles, the size of each individual virus is often known. In such cases, the determined particle size can be used to determine the extent of viral aggregation in the sample. This is particularly useful in vaccine development, etc. Furthermore, as the invention provides methods for functionalising particles e.g. viral particles with other components such as smaller molecules (e.g. via the negatively charged polymer), the invention allows their properties to be studied in solution.

Accordingly, the invention provides a method of assessing enveloped viral aggregation in a sample, comprising:

a) functionalizing the enveloped viral particles in the sample with a negatively charged polymer as described herein; wherein the negatively charged polymer comprises an optically detectable label; wherein the individual viruses in the population have a known size;

b) optically tracking motion of the labelled viral particles;

c) determining an average diffusion coefficient for the labelled viral particles in the sample and thereby obtaining an estimate of the particulate size of the labelled viral particles;

d) comparing the known size of the viruses in the population with the estimated particulate size of the labelled viral particles and thereby assessing the extent of viral aggregation in the sample.

Those skilled in the art will recognise that the methods provided herein can be used to assess a variety of viral characteristics. For example, by optical detection and/or tracking of functionalised viral particles in a sample in accordance with the invention, measurement of viral integrity, viral structural asymmetry and the like can be made. As such, the invention further provides a method of assessing viral integrity of enveloped viral particles in a sample, comprising:

a) functionalizing the enveloped viral particles in the sample with a negatively charged polymer as described herein; wherein the negatively charged polymer comprises an optically detectable label; wherein the individual viruses in the population have a known size;

b) optically tracking motion of the labelled viral particles;

c) optionally determining an average diffusion coefficient for the labelled viral particles in the sample and thereby obtaining an estimate of the particulate size of the labelled viral particles;

d) assessing the extent of viral integrity in the sample.

The invention also provides a method of assessing viral structural asymmetry of enveloped viral particles in a sample, comprising:

a) functionalizing the enveloped viral particles in the sample with a negatively charged polymer as described herein; wherein the negatively charged polymer comprises an optically detectable label; wherein the individual viruses in the population have a known size;

b) optically tracking motion of the labelled viral particles;

c) optionally determining an average diffusion coefficient for the labelled viral particles in the sample and thereby obtaining an estimate of the particulate size of the labelled viral particles;

d) assessing the extent of viral structural asymmetry in the sample.

In the various aspects and embodiments of the invention described herein, enveloped viral particles typically comprise a virus as described herein. The polyvalent cation used in such methods is typically as described herein. The negatively charged polymer used in such methods is typically as described herein. The particle is typically functionalized as described herein. Furthermore, the methods often further comprise the additional steps of binding the functionalized virus particle to a host cell and/or releasing the polymer from the functionalized particle by contacting the functionalized particle with a chelating agent for the polyvalent cation as described herein.

The methods of the invention can be readily put into practice and as such the invention also provides a kit comprising:

(i) a particle having a negatively charged surface and a lipid coating;

(ii) a negatively charged polymer; and (iii) a polyvalent cation for binding the polymer to the particle.

The kit often contains a particle as described herein, a negatively charged polymer as described herein, and a polyvalent cation as described herein. The kit may also comprise further components, such as packaging and instructions for use.

The following Example illustrates the invention. The Example does not, however, limit the invention in any way. In particular, there are many methods of detecting particle functionalization and/or in optically tracking particles, isolating enveloped viral particles from a sample, quantifying enveloped virus particles in a sample, and assessing enveloped viral aggregation in a sample, etc, and so a negative result in any specific assay is therefore not determinative.

EXAMPLE

Detection of viruses is an essential requirement for diagnostic tests. This Example introduces a novel optical approach for single-virus detection, using calcium chloride and fluorescently labelled DNA to rapidly and simply label intact enveloped virus particles. The labelled viruses are extremely bright, allowing individual fluorescent virus particles diffusing in solution to be localised with nanometre precision in a single-particle tracking assay. In this way, the diffusion coefficients and estimated diameters of the diffusing viruses are used as an observable for virus detection. The inventors have demonstrated the feasibility of the assay using multiple different virus types and shown that this approach, with single virus sensitivity, is more rapid than the currently available antigen-based tests (results available within 1 minute). This labelling and detection strategy scales favorably to large numbers of targets or large numbers of clinical samples. Further, this technique can be broadly applied to the direct detection of a wide range of other pathogenic targets.

INTRODUCTION

Infectious diseases caused by viruses represent a huge global public health concern, causing many thousands of deaths annually. Notable human diseases caused by viruses include HIV, influenza, Ebola haemorrhagic fever, hepatitis C, dengue, Zika, measles and rabies. Influenza alone results in the deaths of up to 650,000 people every year during annual epidemics (1), with higher death rates recorded during more severe intermittent pandemics such as the 1918 Spanish flu pandemic that killed more than 50 million people worldwide (2). In spite of the high mortality rates associated with these viruses, we do not currently have a fully effective toolkit of diagnostic assays to detect and identify these dangerous pathogens. Rapid viral diagnosis is important for the provision of strain-specific antiviral treatment; particularly as antiviral compounds can often be expensive or toxic. As well as providing targeted therapy, early detection of viruses can also provide a longer treatment window, resulting in reduced treatment costs and morbidity, help prevent transmission, and lead to more efficient disease management and control.

Traditionally, the gold standard for viral detection has been virus culture in eukaryotic cell lines, which is extremely sensitive but takes significant time (7-10 days) (reviewed in 3). Alternative nucleic acid amplification techniques like RT-PCR are also commonly used, which are highly specific and sensitive but take several hours to obtain a result (reviewed in 3). Viral diagnostics can also be complicated by the presence of multiple genetic variants, for example, four major types of influenza viruses, A, B, C and D, exist. Influenza A viruses are further divided into subtypes based on the antigenic properties of two proteins on the surface of the virus, the haemagglutinin (H1-18) and the neuraminidase (N1-11). These subtypes can then be further broken down into different strains. Antigen-based rapid diagnostic tests that use antibodies to target viral proteins are available for a small subset of viruses such as influenza and respiratory syncytial virus (RSV). These tests are relatively quick (taking less than 30 minutes). However, they are limited by variable detection sensitivity (i.e. the proportion of positive cases that are correctly identified, this can be as low as 62.3% (4)), large numbers of false positives or negatives due to variations in viral load or the improper use of swabs, and can only distinguish between the major influenza types A and B.

Viral diagnostic methods can also be based on the direct quantification and identification of intact virus particles. Flow cytometry-based virus quantification was first described for baculovirus particles (5,6) and has since been used to quantify a variety of other viruses with differing morphologies and genome sizes (reviewed in 7). Flow cytometry techniques make use of fluorescent dyes that bind non-specifically to viral DNA or RNA such as SYBR Green 1 (8) or DAPI, or to viral proteins (9), all of which require at least a 30 minute incubation period for efficient virus labelling prior to virus quantification. Most viruses are too small to be visualised directly by conventional light microscopy, however direct negative stain transmission electron microscopy (TEM) images have been used since the 1940s (10) as an important tool to image individual virus particles and quantitatively determine virus concentrations. Due to the high costs and amount of space required for a TEM instrument this is still only available in certain facilities. Therefore, despite significant progress in the development of viral diagnostics there is still an urgent need for detection methods that meet the criteria of being easy to use, sensitive, specific, rapid and cheap.

In this study, we have established a novel imaging-based method to detect enveloped viruses. We have used calcium chloride ($CaCl_2$) and fluorescent DNA to rapidly and simply label intact virus particles and detected them in a single-particle tracking assay. This approach allowed us to detect viruses more rapidly than the currently available antigen-based tests (with our results being available within one minute), and worked on all enveloped viruses tested. No amplification or purification steps were required as viruses could be detected directly in complex solutions such as cell culture media and allantoic fluid. In addition, fluorescently labelled virus particles maintained their ability to bind to host cells and labelling could be fully reversed by EDTA addition. Our technique can consequently be combined with further downstream analysis and characterisation of viruses, as demonstrated by a virus counting assay using a simple optical fluidics system. We therefore provide a novel tool for the rapid detection of multiple enveloped virus types; the methods and analytical techniques developed here are also applicable to the development of assays to detect many other pathogenic viruses.

RESULTS

Calcium Chloride Labelling and Single-Particle Tracking as a Novel Method for Virus Detection Our study began with a serendipitous discovery while investigating methods of fluorescently labelling intact influenza virus particles. We observed that brief incubations of virus particles with short, fluorescently-labelled, non-specific DNAs in the presence of high concentrations of $CaCl_2$ generated bright fluorescent particles that diffused slowly in solution, and resembled labelled viral particles. The fluorescent particles were extremely bright, pointing to the presence of multiple fluorescent DNA molecules per particle, and diffused much more slowly than free DNAs, which, due to their small size (only a few nm), diffused so rapidly their motion blurred out and merely contributed to the overall background of the sample.

Figure 1:
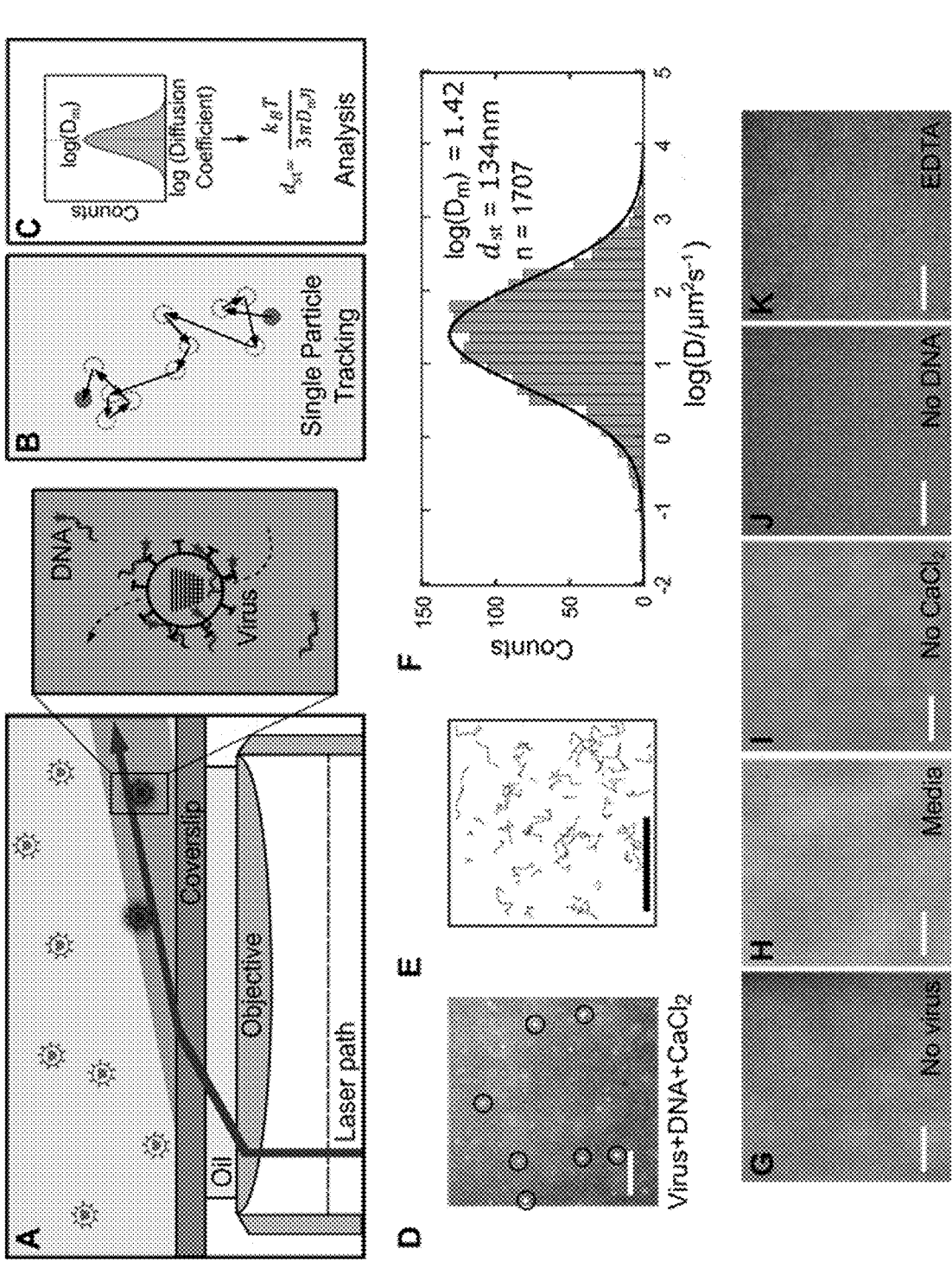
FIG. 1 shows detection of fluorescently-labelled influenza virus using single-particle tracking analysis.

To establish whether the slowly diffusing particles were indeed labelled viral particles, we studied their mobility and number using single-particle tracking (reviewed in 11). In this assay, fluorescently-labelled particles were observed using a widefield microscope with variable angle epifluorescence microscopy (VAEM) to reduce the background signal (12) (FIG. 1A). Single-particle tracking software was then used to track the bright and slow-moving particles (FIG. 1). By localizing visible peaks and associating nearby localizations in subsequent frames with each other, the two-dimensional paths of the diffusing particles were reconstructed for the duration of their visibility in the focal plane. The diffusion coefficients of the tracked particles were then plotted on a histogram and the mean diffusion coefficient ($D_m$) was used to give an estimate of the average diameter of the diffusing particles ($d_{st}$) using the Stokes-Einstein relation (FIG. 1C and equation 5). Thus, the diffusion coefficients and Stokes' diameters obtained from single-particle tracking experiments could be used as an observable for particle detection.

Initially, we fluorescently labelled the spherical H1N1 A/Puerto Rico/8/1934 (PR8) strain of influenza by adding $5.25\times10^6$ PFU/mL PR8 to 0.65M $CaCl_2$ and 1 nM Atto647N-labelled DNA and incubating for one minute; imaging of the sample showed the presence of multiple bright, trackable spots in the field-of-view (FIG. 1D). These spots were tracked simultaneously (FIG. 1E) and the diffusion coefficients were calculated for each track (FIG. 1F). Fitting a Gaussian to the logarithm of the diffusion coefficients (D [$\mu m^2$/s]), gave a mean diffusion coefficient log($D_m$) of 1.42, which provided a Stokes' diameter of 134 nm. Our results were also consistent with the tracking of commercial, fluorescently-labelled microspheres of a similar size. Microspheres of 110 nm in diameter were diluted in water and sonicated to prevent aggregation before being imaged (FIG. 8A) and tracked (FIG. 8B). The resulting diffusion coefficient histogram gave a mean diffusion coefficient log($D_m$) of 1.96, which gave a mean diameter ($d_{st}$) of 108 nm (FIG. 8C). We confirmed that our single-article tracking assay and analysis could differentiate between diffusing objects of different sizes by carrying out a similar experiment with 46 nm microspheres, which gave a value for log($D_m$) of 2.42, providing a mean diameter of 48 nm (FIG. 8D-F).

In order to verify the size and shape of a typical spherical influenza strain, we stained an A/Aichi/68 (X31) virus sample and imaged it using transmission electron microscopy (FIG. 9A). Multiple virus particles, roughly spherical in shape and representing a range of different sizes, were observed (FIG. 9B). We measured the size (average of major and minor axes) (FIG. 9C) of 119 particles and plotted a histogram of the mean diameters (FIG. 9D). The histogram showed a broad distribution of virus sizes, with the largest number of particles (36) falling into the 120-140 nm diameter range. This result was consistent with the results from our single-particle tracking assay, which gave a mean diameter of 134 nm for the fluorescently-labelled particles, as well as with previous TEM or cryo-electron microscopy studies of influenza particles in the literature, which show that spherical strains generally consist of small spheres or ovoid particles of approximately 120 nm in diameter (13-17).

To confirm that the signal we observed in our assay was specific to fluorescently labelled PR8 virus particles, we replaced the virus with either water or minimal essential media (MEM) from mock-infected host cells. No signal was observed in the absence of virus (FIG. 1G&H). Substitution of either the fluorescent DNA (FIG. 1I) or $CaCl_2$ (FIG. 1J) with water also resulted in no signal, indicating that they were both essential requirements for fluorescence labelling to occur. Interestingly, addition of the calcium chelator EDTA to the sample well during observation of fluorescently labelled virus particles immediately eliminated the signal, suggesting that the labelling is reversible (FIG. 1K). Taken together, we have established that the bright, slow-moving particles we observe after incubation of influenza virus with $CaCl_2$ and DNA are single, labelled viruses.

Figure 2:
FIG. 2 shows how detected tracks increase with increasing DNA concentration, calcium chloride concentration, virus concentration and incubation time.

Virus Labelling Requires Calcium Chloride, a Fluorescent Nucleic Acid and a Viral Envelope In order to test the minimal time required to carry out our assay we adjusted the incubation times of the virus with $CaCl_2$ and fluorescent DNA. During sample preparation, unlabelled virus stock was added to a mixture of $CaCl_2$ and DNA (time zero), after which the sample was transferred into the well of a glass slide placed on the microscope (FIG. 2A). The sample was illuminated and a 33-second movie of the viruses diffusing in solution was acquired, resulting in an overall minimal assay time of ~1 minute (FIG. 2A). Subsequent data analysis, taking approximately 20 seconds, was then carried out. Bright, trackable virus particles were observed after this minimal time (one minute), and the number of tracks continued to increase with longer incubation times until 15 minutes (FIG. 2B&C). An incubation time of 20 minutes resulted in a decrease in the number of detected tracks, possibly due to overcrowding effects resulting in overlapping tracks being discarded from the analysis. Using our assay, preparation, visualisation and tracking of virus particles is possible more rapidly than any currently available antigen-based tests, which generally require approximately 30 minutes to obtain a result.

For optimisation of our virus detection conditions, we varied the concentrations of each component of our assay. As expected, the number of tracks detected in the assay increased with increasing DNA, $CaCl_2$ and virus concentration, albeit with differing rates of increase (FIG. 2D-F). Effective virus detection (defined as >400 tracks detected during a 1000 frame acquisition at 30 Hz on the basis that the minimum number of tracks obtained in any of our experiments was 487 (see FIG. 13 later)), was observed at 1 nM DNA, 0.09M $CaCl_2$ and $5.3\times10^6$ PFU/mL PR8 virus for each titration series respectively (FIG. 2D-F).

Figure 3:
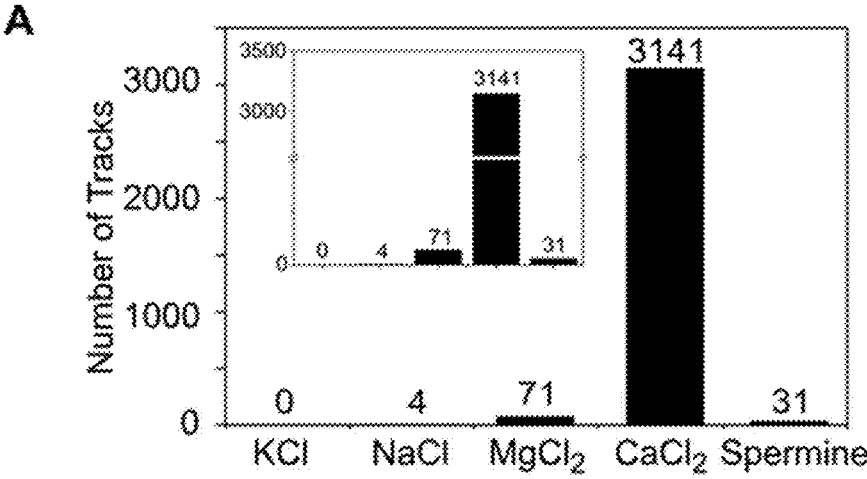
FIG. 3 shows virus labelling using calcium chloride, a fluorescent nucleic acid and a viral envelope.
Figure 3:
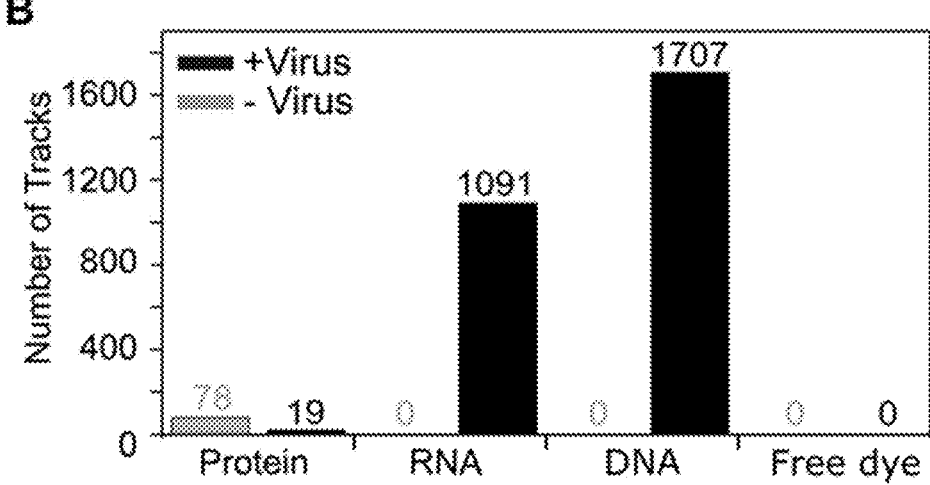
Figure 3:
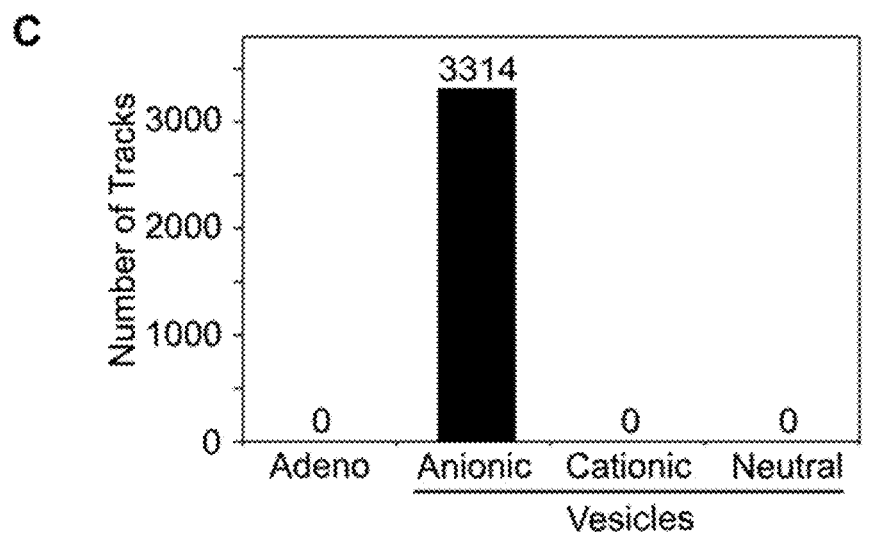

To investigate the nature of the ionic species required for fluorescence labelling to occur, $CaCl_2$ was replaced with KCl, NaCl, $MgCl_2$ or the cationic polyamine spermine, which has an overall ionic charge of +4. PR8 virus was added to 1 nM Atto647N-labelled DNA and 0.65M KCl, NaCl, $MgCl_2$, $CaCl_2$ or 0.32M spermine, and viruses were tracked in solution. Following analysis, no tracks were detected when KCl or NaCl were used, while a small number of tracks were detected when $MgCl_2$ or spermine was used (71 and 31 from a 1000-frame acquisition movie respectively; FIGS. 3A and 10A). In contrast, when $CaCl_2$ was used, a large number of bright trackable particles were observed in the field of view (3141 tracks from a 1000 frame acquisition movie; FIGS. 3A and 10A). We therefore concluded that using monovalent cations did not result in the same efficiency of labelling as addition of $Ca^{2+}$ ions. Other polyvalent cations (divalent cation ($Mg^{2+}$) or a polyanionic compound with higher valency (spermine with +4)) allowed tracking of particles, but at a lower level than $Ca^{2+}$.

We also found that it was possible to label virus particles with either fluorescent DNA or RNA. We also tested labelling with a fluorescently-labelled protein (the Klenow fragment of DNA Polymerase; FIGS. 3B and 10B). Increased labelling with the polynucleotides was observed, suggesting that efficient fluorescence labelling is promoted by the presence of a nucleic acid. To eliminate the possibility that the nature of the dye was responsible for the labelling process we attempted virus labelling and detection using unconjugated Atto647N dye (a non-cyanine dye) not attached to a nucleic acid, which did not result in any fluorescent virus particles (FIG. 3B). In addition, DNA labelled with an alternative dye from the cyanine family, Cy3B, was able to bind to virus particles in the presence of $CaCl_2$ (FIG. 11). We were also able to detect viruses by adding two DNA species, labelled with either Atto647N or Cy3B, simultaneously. Fluorescent viruses diffusing in solution were observed in both channels (illuminated by 532 nm and 640 nm excitation lasers; FIG. 11A&B) and 26% of virus particles were tracked in both channels simultaneously (FIG. 11C). This does not represent the actual number of doubly-labelled viruses (see FIG. 6 later), as particles for which one or both of the trajectories in each channel don't fulfil the exclusion parameters set for the tracking analysis, such as exclusion radius and maximum frame gap (see materials and methods), were discounted.

Influenza viruses are classified as enveloped viruses, in which the outer layer of the particle is a lipid membrane derived from the infected host cell. To study the requirement of a lipid membrane for efficient virus labelling, we tested a sample of adenovirus, which is a medium-sized (~100 nm diameter) non-enveloped virus responsible for a wide range of illnesses in humans, ranging from mild respiratory infections to life-threatening multi-organ disease in people with weakened immune systems. We added $3.3\times10^{11}$ PFU/mL chimpanzee adenovirus (18) to 0.65M $CaCl_2$ and 1 nM Atto647N-labelled DNA; however no labelled virus particles were observed in the field-of-view and no tracks were detected (FIGS. 3C and 10C). Next, we did a similar experiment using 200 nm vesicles containing 25% anionic lipids (giving an overall negative charge), and found that we could observe and track bright particles diffusing in solution (FIGS. 3C and 0C). When cationic or neutral 200 nm vesicles were used in place of the anionic vesicles, no tracks were detected. Without being bound by theory, this suggests that a lipid bilayer may be a necessary requirement for virus labelling to occur, and that $CaCl_2$ mediates an interaction between the negatively charged viral lipid membrane and the negatively charged phosphates of the fluorescently labelled nucleic acid.

Detection of Multiple Virus Types and Strains

To show that our virus detection technique was broadly applicable to all influenza viruses, we tested several different strains. In humans, the two major types of influenza responsible for disease are known as A and B, and influenza A viruses are further divided into subtypes designated H1-18 and N1-11, which can be further broken down into different strains. In addition to the PR8 strain analysed previously (FIG. 1D-F), we were able to successfully detect influenza strains H1N1 A/WSN/1933 (WSN), H3N2 A/Aichi/68 (X31) and B/Florida/04/2006 (InfB), by adding them to 0.65M $CaCl_2$ and 1 nM Atto647N-labelled DNA (FIG. 4A-F). The WSN and InfB strains were detected in minimal essential media harvested from infected cells, while X31 was detected in allantoic fluid harvested from infected eggs, demonstrating the versatility of our assay for virus detection in different complex fluids.

Figure 4:
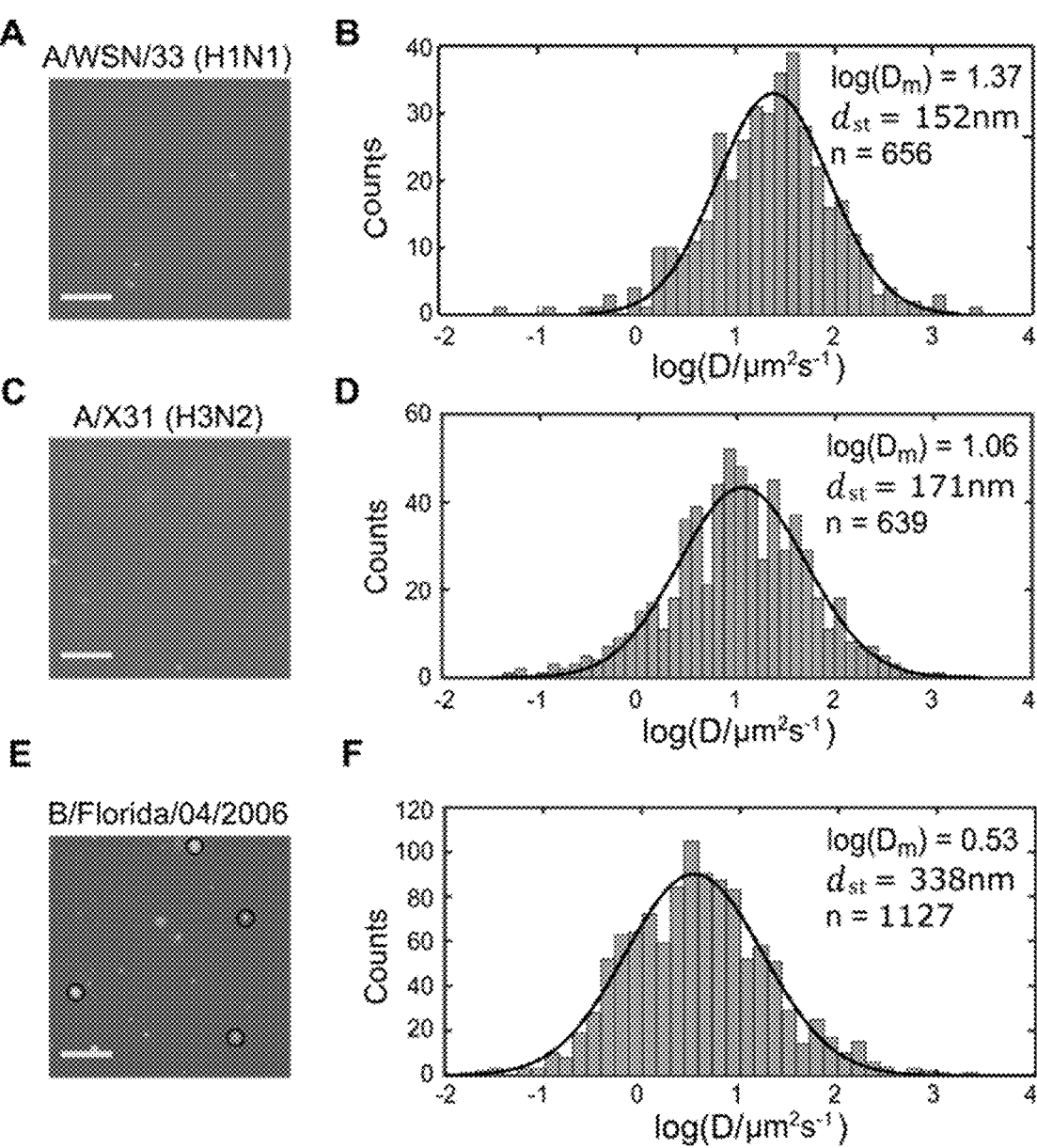
FIG. 4 shows detection of different influenza strains using fluorescent labelling and single particle tracking.

Interestingly, we found that different strains of influenza showed varying degrees of aggregation whilst diffusing in solution (for example, FIG. 4E shows several particles (circled) of InfB that visually appear brighter and larger than others in the field-of-view). Addition of trypsin, a protease enzyme that cleaves peptide bonds on the C-termini of lysine and arginine residues, reduced the aggregation of the virus particles, but did not eliminate it entirely (FIG. 4). The mean log diffusion coefficients obtained for WSN, X31 and InfB in the presence of trypsin were 1.37, 1.06 and 0.53, which gave Stokes diameter values of 152 nm, 171 nm and 338 nm respectively, greater than the sizes expected for single influenza particles (FIG. 4B,D&F). The larger sizes obtained suggested that we were observing a heterogeneous population of diffusing molecules consisting of some monomeric particles and some small aggregates.

In order to investigate this further, we performed simulations to characterise the observed motions of diverse populations of diffusing particles corresponding to viruses of 100 nm (single monomers), 200 nm, 300 nm and 400 nm (larger aggregates). First, we fully modelled movies of particles diffusing with Brownian motion, representing a range of different sizes, within a defined 400×400 pixel field-of-view (19). Examples of some of our simulation movies for small (40 nm), medium (100 nm) and large (300 nm) sized particles are shown in FIG. 12A-C. Motion-blur is apparent for the smaller particles (FIG. 12A&B), and a visual comparison of a particle from the 100 nm simulation movie (FIG. 12D) shows it bears a close resemblance to the image of an actual virus particle (FIG. 12E). The simulation input diffusion coefficients and the values measured by the software were within error (FIG. 12F), validating the simulations as a suitable way to produce data akin to a sample with multiple population sizes. Using the X31 virus sample as an example, which had a $\log(D_m)$ of 1.06 and mean size of 171 nm, we found that a simulation movie consisting of 30% 100 nm particles, 27% 200 nm particles, 23% particles and 20% 400 nm particles gave a mean size of 178 nm when analysed (FIG. 12G). Comparison of the diffusion coefficient plots from the experimental and simulated data show an overall similarity in distribution and minimal differences in mean square deviation, while a comparison with simulated data from 100 nm particles alone did not bear a close resemblance to the experimental data (FIG. 12G). Whilst this is not a unique solution, this supports our hypothesis that the larger Stokes diameter values obtained for some influenza strains was due to aggregation effects.

In addition to being applicable to the detection of a broad range of influenza strains, we tested our labelling and tracking method on two other virus types. First, we were able to label and track the A2 strain of the respiratory syncytial virus (RSV), a Pneumovirus that is a major cause of respiratory tract infections in children worldwide. Like influenza, the virion of RSV is spherical and enveloped within a lipid bilayer in which surface glycoproteins are embedded (FIG. 5A), however RSV particles are larger, ranging from 150-300 nm in diameter (20). Viruses were added to 0.65M $CaCl_2$, 1 nM Atto647N-labelled DNA and 0.0025× trypsin before being imaged and tracked (FIG. 5B-F). The resulting diffusion coefficient histogram gave a mean diffusion coefficient $\log(D_m)$ of 0.94, which provided a mean diameter $(d_{st})$ of 195 nm (FIG. 5G), in good agreement with the size expected from the literature (20,21).

We were also able to label and track the *Autographa californica* nuclear polyhedrosis virus (AcNPV), a rod-shaped baculovirus of insects measuring 40-70 nm in diameter and 250-400 nm in length (FIG. 13A). Viruses were fluorescently labelled before being imaged and tracked (FIG. 13B-F). By modelling the baculovirus particle as an ellipsoid, with a characteristic rotational diffusion that was significantly smaller than the exposure time of our experiment (30 ms), we assumed that the measured motion was isotropic (22). In this way, we were able to use the observed trajectories to calculate a diffusion coefficient histogram (equation 4, Materials and Methods) to give a mean diffusion coefficient $\log(D_m)$ of 0.26 (FIG. 13G). By assuming a mean axial ratio of 5.9 (calculated by dividing a mean value of 325 nm for the long axis of the baculovirus particle by 55 nm for the short axis (22)), we obtained an approximate size of 91 nm by 536 nm for our baculovirus particles. Similarly to our experiments with influenza, over-estimation of virus size may result from aggregation. Our results thus establish the applicability of our virus detection methods to other enveloped viruses with a more complex geometry.

Fluorescently Labelled Virus Particles Maintain their Ability to Bind to Host Cells We investigated the ability of influenza virus particles that were fluorescently labelled using $CaCl_2$ to bind to mammalian cells. Fluorescent PR8 virus was incubated with MDCK cells to allow adsorption, before the cells were fixed, stained with DAPI to show cellular DNA in the cell nucleus, and imaged (FIG. 14). Small punctate spots were observed on the cell surface around the nuclei using 640 nm laser excitation, suggesting that fluorescently-labelled virus particles were able to attach to host cells (FIG. 14A&B). These spots could not be seen when either PR8 (FIG. 14C), $CaCl_2$ (FIG. 14D) or fluorescent DNA (FIG. 14E) were excluded from the experiment. The ability of the labelled viruses to bind to host cells suggests that virus particles labelled using calcium chloride and fluorescent DNA still maintain their structural integrity, and that the DNA does not completely obscure the viral haemagglutinin proteins required for host cell receptor binding on the virus surface.

Counting Fluorescently-Labelled Virus Particles Using Fluidics

A simple and rapid method for fluorescent labelling of virus particles has multiple downstream applications. In order to demonstrate the applicability of our technique for virus counting (6,7), we used $CaCl_2$ and DNA to label and directly quantify single virus particles. We constructed a simple fluidics system where the fluorescent sample was pumped through a narrow microslide channel and illuminated using a confocal microscope with alternating red and green laser excitation (shown schematically in FIG. 6A). As the fluorescent particles passed through the confocal volume, a burst of fluorescence was detected by two avalanche photodiodes detecting red and green fluorescence, and custom-written software was used to count the number of bursts above background (see materials and methods and FIG. 6A). As an initial proof-of-principle, we tested the 110 nm fluorescent microspheres, which showed frequent bursts of simultaneous red and green fluorescence as the spheres passed through the illuminated volume (FIG. 6B).

Next, we used our fluidics system to detect PR8 virus that was simultaneously labelled with green or red fluorophores using $CaCl_2$. Only low-level background fluorescence was detected when virus was excluded from the sample (FIG. 6C, top panel), however, when labelled virus was flowed through the channel bursts of fluorescence showing simultaneous peaks of green and red fluorescence were observed (>90% of detected bursts showed both red and green labelling) (FIG. 6C second panel & 6D). The frequency of bursts detected increased when increasing concentrations of the virus was added (FIG. 6C, third and fourth panels). The fluorescence intensity traces were then analysed using a threshold-based sliding window algorithm to detect events, combined with a Gaussian peak fitting process to identify the height, width and location of individual peaks corresponding to fluorescent bursts. As expected, the number of detected virus particles increased linearly with increasing concentration (intercept (y)=−0.03±0.04) (FIG. 6E).

Both the microspheres and the virus particles were extremely bright, giving rise to many burst events exceeding 1000 counts (FIG. 6B&C). When we quantified the mean fluorescence intensity arising from the particles, we found that the intensity for the virus particles and the fluorescent microspheres were within error (standard deviation from multiple acquisitions) of each other (FIG. 6F). In order to get an estimate of the number of fluorescent DNAs per virus particle we analysed the intensity profiles of surface-immobilised labelled viruses (FIG. 15A). By integrating the area of each intensity peak we obtained a mean intensity value of 3134 a.u. for the virus particles (FIG. 15B&C). By comparison, single DNAs were significantly less bright than immobilised viruses, with a mean intensity value of 94 a.u. (FIG. 15D-F). This gives an average number of 3134/94=33 DNA molecules per virus particle. Overall, the brightness of the virus particles arising from our labelling method is such that it would be useful for viral detection methods based on direct quantification of intact virus particles, such as flow cytometry.

Calcium Labelling of Purified Exosomes

We have also confirmed that the methods of the invention can be used to label purified exosomes.

Exosomes were purified from human keratinocyte cells using an ExoQuick kit (System Biosciences). One sample of purified exosomes was filtered to obtain a homogenous size whilst a second sample was not filtered. Exosomes were double-labelled with 0.65M CaCl$_2$, 1 nM Cy3B-labelled DNA (green channel; 532 nm) and 1 nM Atto647N-labelled DNA (red channel; 640 nm), and were immobilized on a chitosan-treated glass surface before being observed using a wide-field microscope.

Representative fields-of-view (visualized in the green channel; 532 nm) of fluorescently labelled exosomes are shown in FIG. 17 (top panels). Scale bar 10 μm. Merged localisations (overlaid signals from both the red and green channels) are shown in the bottom panels of FIG. 17. Co-localised signals representing double-labelled exosomes are shown in yellow, and white circles represent examples of co-localised particles. The results shown in FIG. 17 confirm that the methods of the invention can be used to label and image particles which are exosomes, in accordance with the discussion herein.

Calcium Labelling of Influenza Viruses Combined with Specific Antibody Labelling.

We have further confirmed that the calcium labelling of influenza viruses in accordance with the methods of the invention can be combined with specific antibody labelling.

Green fluorescent DNAs were used to non-specifically label virus particles immobilized via biotin/neutravidin on the surface of a pegylated (PEG) glass slide. Immobilised viruses were then stained with red fluorescent antibodies specific to the virus strain. A schematic of the setup used is shown in FIG. 18(A).

FIG. 18(B) and FIG. 18(C) show representative results. Panel B shows representative field-of-view of A/Udorn/72 (H3N2) (Udorn) virus particles. A/Udorn/72 virus at a final concentration of 12.5×10$^5$ PFU/mL was added to 0.65M CaCl$_2$ and 1 nM Cy3B-labelled DNA before being immobilized. Viruses were stained with an anti-NA primary antibody and Alexa647-labelled secondary antibody before being observed on a wide-field microscope. FIG. 18(B) shows detection of the labelled particles using a green 532 nm laser (left panel), antibody-staining detected using a red 647 nm laser (middle panel) and merged red and green localisations (shown in the right panel). White circles represent examples of merged localisations. Scale bar 10 μm.

FIG. 18(C) shows corresponding results using 41.2×10$^6$ PFU/mL A/WSN/33 (H1N1) (WSN) virus particles. Viruses were stained with an anti-NP primary antibody and Alexa647-labelled secondary antibody and were labelled and imaged as above. Detection of the labelled particles using a green 532 nm laser is shown in FIG. 18(C) (left panel), antibody-staining detected using a red 647 nm laser (middle panel) and merged red and green localisations (shown in the right panel). White circles represent examples of merged localisations. Scale bar 10 μm.

DISCUSSION

Traditional diagnostic approaches for virus detection such as cell culture and antigen-based tests are often hampered by long waiting times, or limited sensitivity and specificity. In this work, we have demonstrated a novel CaCl$_2$-based fluorescent labelling method and single-particle virus tracking technique that can be used to quickly and simply detect and characterise multiple virus strains. The short preparation time and requirement for only a small sample input offered by our approach makes it an exciting alternative for virus diagnostics.

Mechanism of Calcium-Mediated Virus Labelling

Our CaCl$_2$-based fluorescent labelling method worked on all enveloped virus strains tested, including both influenza A and B subtypes and multiple different influenza strains, as well as the unrelated respiratory syncytial virus and the AcNPV baculovirus. Conversely, no tracks were detected using a non-enveloped adenovirus sample. We were also able to detect fluorescently labelled anionic, but not cationic or neutral, lipid vesicles. Taken together, this suggests that the negative charge of the virus is advantageous for fluorescent labelling to occur. Our observations also established that fluorescent labelling of viruses is promoted by both CaCl$_2$ and a fluorescently-labelled nucleic acid, which can be either DNA or RNA.

The interactions of calcium ions with lipid membranes have been probed by a variety of experimental methods, including fluorescent spectroscopy, dynamic light scattering and zeta potential measurements, in combination with computational molecular dynamics simulations (reviewed in 23). It is generally accepted that the presence of calcium rigidifies and orders lipid bilayers, for example by causing conformational changes in lipid headgroups, ordering of acyl chains, and lipid dehydration (reviewed in 23). Studies have demonstrated that calcium binds primarily to the phosphate groups of phospholipids, and simulations indicate that calcium is able to cluster phospholipid molecules via ion-bridges (24,25), binding at least three lipid molecules concurrently (23,25). Without being bound by theory, it is plausible that in our experiments this stoichiometry is maintained, and one of the lipid molecules is replaced with a negatively charged phosphate group from the DNA/RNA. We therefore propose a model for our labelling method that suggests that the Ca$^{2+}$ ions derived from calcium chloride facilitate an interaction between the negatively charged polar heads of the viral lipid membrane and the negatively charged phosphates of the nucleic acid, possibly by binding two lipid molecules and a phosphate at the same time (FIG. 7). We cannot exclude the possibility that CaCl$_2$ treatment also weakens the viral membrane and creates small pores or invaginations (26) that allow internalisation the nucleic acid, however the instantaneous loss of fluorescent signal upon EDTA addition suggests that the labelling is more likely to be external to the virus particle. We can draw parallels between our labelling strategy and bacterial transformation, the process whereby DNA is taken up by the bacterial cell (27). Positively charged Ca$^{2+}$ ions are thought to mediate DNA uptake by shielding negative charges on the bacterial surface and the DNA, thereby allowing DNA to adhere to the cell surface (28).

Detection of Viral Aggregation

A key observation made during our testing of multiple different influenza strains was that different strains tended to aggregate to different degrees, for example, the H1N1 PR8 strain showed the least amount of aggregation, and the influenza B virus the most (FIG. 4). This suggested that the aggregation was not a consequence of our labelling method, but rather an intrinsic feature specific to some influenza viruses. Auto-aggregation of influenza was initially suggested based on the observation that the increase in titre of virus suspensions treated with trypsin was due to dis-aggregation (29). In support of this, we found that addition of a low concentration of trypsin in our assay reduced the aggregation to the extent that we were able to successfully track all virus strains tested. In addition, electron microscopy sometimes shows influenza viruses clustered together, although it is not clear whether this is an artefact of preparation or the natural state of the virus. Our results suggest that influenza viruses tend to aggregate independently, in a strain-specific manner.

Viral vaccine production requires stable virus preparations, with producers needing to assess the purity, titre and aggregation of the virus at different stage of the manufacturing process. This is important for optimising virus yield and accurately quantifying the final dosage. Our assay provides a simple and rapid method for quantitating whole virus particles (FIG. 6), which is particularly important in the production of inactivated vaccines, for which virus titre cannot be estimated using traditional infectivity assays. The method also represents a quick and rapid way of assessing virus aggregation, which is not available through alternative methods.

Use of Calcium-Mediated Labelling for Viral Detection and Diagnostics

The fluorescent-labelling technique presented here has several advantages over existing virus detection techniques. Viruses could be detected directly in complex biological fluids such as MEM or allantoic fluid from eggs, without the need for purification or amplification steps. The labelling was instantaneous and the signal from diffusing fluorescent viruses could be observed and analysed very rapidly (e.g. in just over one minute (FIG. 2)). This timescale is significantly shorter than the conventionally used fluorescent dyes used to label viruses for flow cytometry, such as SyBR Green 1 and DAPI, which require an incubation period of at least 30 minutes (7,9). In addition, the technique is simple and cost-effective, and does not require expensive reagents. Only a small sample volume (20 μl) is required, and we were able to effectively detect RSV virus at a concentration of $7.0 \times 10^2$ PFU/mL, comparable in range with RT-PCR assays which can detect $10^1$-$10^2$ copies of RNA transcript/mL (30).

Following labelling, the virus particles had a similar intensity to bright, commercial fluorescent microspheres, and we confirmed that the bright signal was due to the presence of multiple DNA molecules per particle. This bright signal is a beneficial feature for efficient and rapid single-particle tracking analysis. We also expect this technique to be widely applicable in many other research areas that require fluorescently labelled virus particles; for example, we have demonstrated its usefulness for direct virus counting in a proof-of-principle assay (FIG. 6), offering a potential alternative to infectivity assays. Because the virus particles are so bright it will be possible to observe them in a wide variety of conventional fluorescence microscopes. Furthermore, we have shown that the virus particles maintain their ability to bind to cells post-labelling, making this method an attractive option for in vivo imaging studies of virus infection.

In this study we have focused on the use of $CaCl_2$ to mediate the interaction of virus particles and fluorescently labelled DNA, however we envisage that this method can also be used as a general biochemical tool for virus surface functionalization. For example, our method can be used to add biotin or reactive groups of choice to the exterior of viruses, offering a useful alternative for viral down assays and purification protocols. The assay can also be combined with strain-specific labelling approaches, which could represent a breakthrough in viral diagnostics. The methods and analytical techniques developed here are therefore applicable to the development of assays to study and detect many other pathogenic viruses.

Regarding the combination of the assay with strain-specific labelling approaches, we have successfully managed to pull down viruses using the calcium chloride method (and image them in one colour), and use strain-specific antibodies to label immobilized viruses (imaged in a second colour).

Thus, FIG. 16 shows specific antibody labelling of influenza viruses.

FIG. 16A is a schematic representation of the assay, where fluorescently labelled (green fluorophore), biotinylated DNAs were used to non-specifically label and pull-down virus particles onto the surface of a glass slide. A/WSN/33 virus (WSN) at a final concentration of 49.5×106 PFU/mL was added to 0.65M $CaCl_2$ and 1 nM Cy3B-labelled DNA before being incubated on a pegylated (PEG) slide for 10 minutes. The slide was then washed with 1M $CaCl_2$ before being observed using a wide-field microscope. FIG. 16B is a representative field-of-view of immobilised virus particles (left panel), or a negative control lacking virus (right panel), on the surface of a glass slide, detected using a green laser (532 nm).

FIGS. 16C and 16D demonstrate the use of strain-specific antibodies to label the immobilized viruses so that specific strains could be imaged in a second colour. Thus, FIG. 16C is a representative field-of-view of immobilized A/Udorn/72 (H3N2) virus particles (left panel), or a negative control lacking virus (right panel), stained with a fluorescent antibody (red fluorophore) specific to the A/Udorn/72 virus strain, detected using a red laser (647 nm). FIG. 16D is a representative field-of-view of immobilized A/WSN/33 (H1N1) virus particles (left panel), or a negative control lacking virus (right panel), stained with a fluorescent antibody (red fluorophore) specific to the A/WSN/33 virus strain, detected using a red laser (647 nm).

Materials and Methods

Viruses

H1N1 A/WSN/1933 (WSN), H1N1 A/Puerto Rico/8/1934 (PR8) and B/Florida/04/2006 (InfB) influenza viruses were grown in Madin-Darby bovine kidney (MDBK) or Madin-Darby canine kidney (MDCK) cells. The cell culture supernatant (Minimal Essential Media, Gibco) was collected and the viruses were titred by plaque assay. Titres of WSN, PR8 and InfB were $3.3 \times 10^8$ plaque forming units (PFU)/mL, $1.05 \times 10^8$ PFU/mL and $2.1 \times 10^8$ PFU/mL respectively. H3N2 A/Aichi/68 (X31) was grown in embryonated chicken eggs and titred by plaque assay ($4.5 \times 10^8$ PFU/mL). The A2 strain of RSV was grown in Hep-2 cells and titred by plaque assay ($1.4 \times 10^5$ PFU/mL). All influenza and RSV virus stocks were inactivated by shaking with 0.2% formaldehyde for a minimum of 24 hours before use. Recombinant baculovirus derived from the *Autographa californica* nuclear polyhedrosis virus was produced using the Multibac system (31) and was of unknown titre. Chimpanzee adenovirus ChAdOxl-GFP was grown in HEK293 cells and titred by plaque assay ($1.1 \times 10^{12}$ PFU/mL) (18).

Fluorescent Microspheres, DNA, RNA, Protein and Vesicles

Fluorescent microspheres with diameters of 110 nm and 46 nm were purchased from Life Technologies. The microspheres were diluted in water and sonicated for 15 minutes on ice prior to use. Single-stranded oligonucleotides labelled with either ATTO647N, Cy3B or Cy3 dyes were purchased from IBA (Germany).

The DNA sequences used were 64mers with the sequences 5'-GAAATTGTTATCCGCTCTCACAATTC-CACACATTATACGAGCCGAAGCATAAA GTGT-CAAGCCX-3', where X=T-Atto647N (SEQ ID NO:19), and 5'-AGGCTTGACACTT-TATGCTTCGGCXCGTATAATGTGTGGAATTGT-GAGAGCGG ATAACAATTTC-3', where X=T-Cy3B (SEQ ID NO:20). The RNA sequence used was a 34mer with the sequence 5'-AGUAGAAACAAGGAGUUXU-UUGAACAAACUACUU-3', where X=U-Cy3 (SEQ ID NO:20). The fluorescently-labelled protein was the Klenow fragment of *E. coli* DNA polymerase I (32), site-specifically labelled at position 550 with ATTO647N and 744 with Cy3B.

Lipid vesicles of 200 nm in diameter were prepared as described previously (33), using extrusion with a 200 nm pore size. Anionic lipid vesicles were composed of 75% 1,2-dioleoyl-sn-glycero-3-phosphocholine (DOPC) and 25% 1-palmitoyl-2-oleoyl-sn-glycero-3-phosphate (POPA), cationic vesicles were composed of 50% DOPC and 50% Ethyl-phosphocholine, and neutral vesicles were composed of soybean phosphocholine. Vesicles at a concentration of 10 mg/mL were stored in 100 mM KCl (pH 7.5), 50 mM MOPS and 1 mM $MgCl_2$, before being diluted, labelled and imaged.

Sample Preparation

Unless otherwise stated, virus stocks (typically 1-5 μL) were diluted in 0.65M $CaCl_2$ and 1 nM fluorescently-labelled DNA in a final volume of 20 μL (final virus concentrations are indicated in the figure legends). The sample was immediately placed in a well on a glass slide and imaged using variable angle epifluorescence microscopy (VAEM). The laser illumination was focused at a typical angle of 52° with respect to the normal, sufficiently above the surface of the glass slide to minimise background from unbound DNA settled on the surface (~3-15 μm above surface). Typical acquisitions were 1000 frames, taken at a frame rate of 30 Hz, with laser intensities kept constant at 0.78 $kW/cm^2$. In experiments where trypsin was added 0.5 μL of a 0.05× stock of recombinant trypsin (TrypLE™ Express Enzyme, Thermo-Fisher Scientific) was added to the final sample volume of 20 μL. In experiments where EDTA was added a final concentration of 100 mM EDTA was added directly to the well during imaging.

Instrumentation

Single-particle tracking experiments were performed on a commercially available fluorescence Nanoimager micro-scope (Oxford Nanoimaging, https://www.oxfordni.com/). Briefly, a green (532 nm) and a red (635 nm) laser were combined using a dichroic mirror and coupled into a fibre optic cable. The fibre output was focused into the back focal plane of the objective (100× oil immersion, numerical aperture 1.4) and, for VAEM, displaced perpendicular to the optical axis resulting in a highly oblique subcritical incident angle on the sample to decrease background fluorophore excitation. Fluorescence emission was collected by the objective, separated into two emission channels and imaged onto a sCMOS camera (Orca flash V4, Hamamatsu).

Data Analysis

For single-particle tracking analysis, the Nanoimager software suite was first used to localize the fluorescent molecules in each frame by finding intensity peaks that were significantly above background, then fitting the detected spots with a Gaussian function. The Nanoimager single-particle tracking feature was then used to map trajectories for the individual virus particles over multiple frames, using a pre-defined maximum step distance (the maximum distance that a particle may travel between frames for it to be considered the same particle) and nearest-neighbor exclusion radius (particles in the same frame who are closer than the exclusion radius are omitted from tracking due to inability to assign them to tracks). These parameters were used to maximise the track count; the maximum step distance was used to exclude particles that were diffusing much more quickly than the predicted size of virus particles (e.g. free dye) and the exclusion radius was used to exclude tracks which crossed over, which could lead to ambiguity in trajectory assignment. The 110 nm and 46 nm microspheres were used to calibrate the optimum parameters as a function of the expected distance travelled between frames and the spatial density of localisations. The maximum step distance was taken as $$\text{Maximum step distance} = \gamma \sqrt{<(\Delta x_{Pred})^2>} \tag{1}$$

where $\gamma$ was set to 5 in order to minimise false trajectory assignment, and $$<(\Delta x_{Pred}^2)> = 4D_{Pred}t_{exp} \tag{2}$$

where $D_{Pred}$ is the predicted diffusion coefficient of a spheri-cal particle of the expected size in the solution of interest and $t_{exp}$ is the exposure time (typically 30 ms). The exclusion radius was taken as $$\text{Exclusion Radius} = 0.1 \sqrt{\frac{1}{N}} \tag{3}$$

where N is the average number of particles per unit area, calculated by averaging the number of particles per unit area in each frame of a movie. The channel with the largest number of localisations was used to calculate the exclusion radius. In cases where the exclusion radius was smaller than the maximum distance, in samples with a high density of fluorescent particles for example, both parameters were set to the maximum distance. In the case of multicolour track-ing, a particle observed in both channels was considered to be co-localised if simultaneous localisation in the red and green channels was separated by less than 200 nm.

The trajectories were then used to calculate a diffusion coefficient for each track using the equation:

$$D = \frac{\sqrt{<(\Delta x)^2>}}{6\Delta L\epsilon} \tag{4}$$

where D is the diffusion coefficient, $<(\Delta x)^2>$ is the mean square displacement, t is the time and c is a correction factor to account for a non-zero exposure time (34). A histogram of the natural log diffusion coefficient for each track was then plotted using a custom-written MATLAB script. The histo-gram was fitted with a Gaussian function and the diffusion coefficient which corresponded to the curve peak was taken to be the sample mean ($D_m$). The Stokes' diameter ($d_{st}$) was then calculated using:

$$d_{st} = \frac{k_B T}{3\pi D_m \eta} \tag{5}$$

where T is the temperature, $D_m$ is the mean diffusion coefficient and $\eta$ is the viscosity of the solution. The sample temperature was obtained from the microscope sensors and the viscosity of the solution was corrected for the presence of calcium chloride (35).

Simulations

Movies simulating the unconfined diffusion of viruses were produced using existing software (19), with a number of modifications. For each virus particle, an initial position and time at which the particle entered the field-of-view was generated randomly, with the bounds of diffusion set to beyond the field-of-view to simulate unconfined diffusion. The position of each particle was then calculated at 100 sub-steps per frame to simulate the effects of motion blur, using track lengths that followed an exponential distribution. Point spread functions were calculated for each localisation and added to a matrix that formed the final movie, before random noise was added to simulate fluctuations in the background photon intensity. The simulated movies were then analysed using custom-written Matlab software.

Electron Microscopy

H3N2 A/Aichi/68 (X31) virus was visualized by transmission electron microscopy at the Bioimaging Facility of the Sir William Dunn School of Pathology, University of Oxford. Virions were prepared as described previously (36). Briefly, they were fixed with 4% paraformaldehyde, adsorbed onto grids, negatively stained with 2% aqueous uranyl acetate and imaged in a Tecnai 12 transmission electron microscope (FEI, Eindhoven) operated at 120 kV.

Immunofluorescence

MDCK cells were grown on 13 mm coverslips in 24-well plates before being infected with A/Puerto Rico/8/1934 virus at a multiplicity of infection of ~20×10$^6$ PFU/mL. The virus was incubated with 0.65M $CaCl_2$ and 1 nM Atto647N-labelled DNA before being added to the cells. The cells were incubated for 1 hour at 37° C. to allow viruses to adhere before being fixed for 15 minutes in 4% paraformaldehyde and mounted onto glass microscope slides with Mowiol containing DAPI. Cells were viewed using an Olympus Fluoview FV1200 microscope and images processed with ImageJ.

Virus Counting

A custom-built confocal microscope was used for single-particle virus counting experiments (37-39). Fluorescent microspheres with a diameter of 110 nm or fluorescently-labelled A/Puerto Rico/8/1934 virus was flowed through a microslide channel (100 μm high×1 mm wide; Ibidi GmbH) using a syringe infusion pump (Harvard Apparatus, Pump 11 Elite) and illuminated using alternating red (647 nm) and green (532 nm) laser excitation at a modulation frequency of 10 kHz. Bursts of fluorescence corresponding to the passage of each virus particle through the confocal volume were split spectrally onto two avalanche photodiodes detecting red and green fluorescence. Fluorescence data recorded by the avalanche photodiodes was acquired using a custom-written LabVIEW virtual instrument into the single molecule (.sm) format, and converted to plain text using a second virtual instrument. Analysis of the raw time series data was performed using custom-written MATLAB code, which implemented a threshold-based sliding window algorithm to detect events, combined with a Gaussian peak fitting process to identify the height, width, and location of individual peaks. Using a trigger level, re-arming level, minimum event duration, maximum event intensity, and baseline input by the user, the procedure first subtracted the baseline. The trace was then scanned point-by-point, building a map of time points for which the fluorescence intensity exceeds the trigger level without re-crossing the re-arming threshold. To minimise errors in the Gaussian peak fitting process for short-lived events, data were automatically extracted from either side of these events to ensure that a minimum of 10 data points were available to the peak fitting algorithm. Data from each event were fitted using a Gaussian peak fitting procedure, outputting the peak intensity, duration, and position within the trace of each fluorescent event. In rare instances, where the expansion of the event window caused overlap with neighbouring events, fitting errors may occur. To address this issue, the procedure identified overlapping regions, which were then merged. The peak fitting process then identified only the largest peak, and discarded the smaller peaks. Error checking was then performed, removing events that exceeded the maximum expected event duration, and intensity. Descriptive statistics for detected peaks were output for further analysis and presentation in Origin.

Intensity Profile Analysis

A/Puerto Rico/8/1934 (H1N1) virus particles were fluorescently labelled by incubation with 1 nM biotin-conjugated DNA labelled with Atto647N, before being immobilised on the surface of a pegylated glass slide treated with neutravidin. The slide surface was imaged using TIRF (total internal reflection fluorescence) with the laser illumination focused at a typical angle of 53° with respect to the normal. Intensity profiles from 20 pixel slices of the fields of view were taken using the built-in 'plot profile' feature on ImageJ. The intensity peaks were fitted using the 'fitpeaks' function in MATLAB, the local background was subtracted, and the peaks were integrated to give an estimate of the intensity of the peak. Multiple particles were analysed and the mean or median peak area of the resulting histogram was taken as the average particle intensity, which was compared between virus particles and free DNA.

REFERENCES

1. World Health Organsation. (2017).
2. Johnson, N. P. and Mueller, J. (2002) Updating the accounts: global mortality of the 1918-1920 "Spanish" influenza pandemic. *Bull Hist Med*, 76, 105-115.
3. Vemula, S. V., Zhao, J., Liu, J., Wang, X., Biswas, S. and Hewlett, I. (2016) Current Approaches for Diagnosis of Influenza Virus Infections in Humans. *Viruses*, 8, 96.
4. Chartrand, C. and Pai, M. (2012) How accurate are rapid influenza diagnostic tests?*Expert Rev Anti Infect Ther*, 10, 615-617.
5. Stoffel, C. L. and Rowlen, K. L. (2005) Data analysis for a dual-channel virus counter. *Anal Chem*, 77, 2243-2246.
6. Stoffel, C. L., Kathy, R. F. and Rowlen, K. L. (2005) Design and characterization of a compact dual channel virus counter. *Cytometry A*, 65, 140-147.
7. Brussaard, C. P., Marie, D. and Bratbak, G. (2000) Flow cytometric detection of viruses. *J Virol Methods*, 85, 175-182.
8. Marie, D., Brussaard, C. P. D., Thyrhaug, R., Bratbak, G. and Vaulot, D. (1999) Enumeration of marine viruses in culture and natural samples by flow cytometry. *Appl Environ Microbiol*, 65, 45-52.
9. Rossi, C. A., Kearney, B. J., Olschner, S. P., Williams, P. L., Robinson, C. G., Heinrich, M. L., Zovanyi, A. M., Ingram, M. F., Norwood, D. A. and Schoepp, R. J. (2015) Evaluation of ViroCyt® Virus Counter for rapid filovirus quantitation. *Viruses*, 7, 857-872.
10. Nagler, F. P. and Rake, G. (1948) The Use of the Electron Microscope in Diagnosis of Variola, Vaccinia, and Varicella. *J Bacteriol*, 55, 45-51.
11. Shen, H., Tauzin, L. J., Baiyasi, R., Wang, W., Moringo, N., Shuang, B. and Landes, C. F. (2017) Single Particle Tracking: From Theory to Biophysical Applications. *Chem Rev*, 117, 7331-7376.
12. Konopka, C. A. and Bednarek, S. Y. (2008) Variable-angle epifluorescence microscopy: a new way to look at protein dynamics in the plant cell cortex. *Plant J*, 53, 186-196.
13. Harris, A., Cardone, G., Winkler, D. C., Heymann, J. B., Brecher, M., White, J. M. and Steven, A. C. (2006) Influenza virus pleiomorphy characterized by cryoelectron tomography. *Proc Natl Acad Sci USA*, 103, 19123-19127.

14. Yamaguchi, M., Danev, R., Nishiyama, K., Sugawara, K. and Nagayama, K. (2008) Zernike phase contrast electron microscopy of ice-embedded influenza A virus. *J Struct Biol,* 162, 271-276.

15. Booy, F. P., Ruigrok, R. W. and van Bruggen, E. F. (1985) Electron microscopy of influenza virus. A comparison of negatively stained and ice-embedded particles. *J Mol Biol,* 184, 667-676.

16. Nermut, M. V. (1972) Further investigation on the fine structure of influenza virus. *J Gen Virol,* 17, 317-331.

17. Fujiyoshi, Y., Kume, N. P., Sakata, K. and Sato, S. B. (1994) Fine structure of influenza A virus observed by electron cryo-microscopy. *EMBO J,* 13, 318-326.

18. Dicks, M. D., Spencer, A. J., Edwards, N. J., Wadell, G., Bojang, K., Gilbert, S. C., Hill, A. V. and Cottingham, M. G. (2012) A novel chimpanzee adenovirus vector with low human seroprevalence: improved systems for vector derivation and comparative immunogenicity. *PLoS One,* 7, e40385.

19. Uphoff, S., Reyes-Lamothe, R., Garza de Leon, F., Sherratt, D. J. and Kapanidis, A. N. (2013) Single-molecule DNA repair in live bacteria. *Proc Natl Acad Sci USA,* 110, 8063-8068.

20. Bachi, T. and Howe, C. (1973) Morphogenesis and ultrastructure of respiratory syncytial virus. *J Virol,* 12, 1173-1180.

21. Kiss, G., Holl, J. M., Williams, G. M., Alonas, E., Vanover, D., Lifland, A. W., Gudheti, M., Guerrero-Ferreira, R. C., Nair, V., Yi, H. et al. (2014) Structural analysis of respiratory syncytial virus reveals the position of M2-1 between the matrix protein and the ribonucleo-protein complex. *J Virol,* 88, 7602-7617.

22. Han, Y., Alsayed, A., Nobili, M. and Yodh, A. G. (2009) Quasi-two-dimensional diffusion of single ellipsoids: aspect ratio and confinement effects. *Phys Rev E Stat Nonlin Soft Matter Phys,* 80, 011403.

23. Melcrova, A., Pokorna, S., Pullanchery, S., Kohagen, M., Jurkiewicz, P., Hof, M., Jungwirth, P., Cremer, P. S. and Cwiklik, L. (2016) The complex nature of calcium cation interactions with phospholipid bilayers. *Sci Rep,* 6, 38035.

24. Tsai, H. H., Lai, W. X., Lin, H. D., Lee, J. B., Juang, W. F. and Tseng, W. H. (2012) Molecular dynamics simulation of cation-phospholipid clustering in phospholipid bilayers: possible role in stalk formation during membrane fusion. *Biochim Biophys Acta,* 1818, 2742-2755.

25. Pedersen, U. R., Leidy, C., Westh, P. and Peters, G. H. (2006) The effect of calcium on the properties of charged phospholipid bilayers. *Biochim Biophys Acta,* 1758, 573-582.

26. Thomas, K. J., 3rd and Rice, C. V. (2014) Revised model of calcium and magnesium binding to the bacterial cell wall. *Biometals,* 27, 1361-1370.

27. Mandel, M. and Higa, A. (1970) Calcium-dependent bacteriophage DNA infection. *J Mol Biol,* 53, 159-162.

28. Asif, A., Mohsin, H., Tanvir, R. and Rehman, Y. (2017) Revisiting the Mechanisms Involved in Calcium Chloride Induced Bacterial Transformation. *Front Microbiol,* 8, 2169.

29. Gresser, I. and Enders, J. F. (1961) The effect of trypsin on representative myxoviruses. *Virology,* 13, 420-426.

30. Duchamp, M. B., Casalegno, J. S., Gillet, Y., Frobert, E., Bernard, E., Escuret, V., Billaud, G., Valette, M., Javouhey, E., Lina, B. et al. (2010) Pandemic A(H1N1) 2009 influenza virus detection by real time RT-PCR: is viral quantification useful? *Clin Microbiol Infect,* 16, 317-321.

31. Bieniossek, C., Imasaki, T., Takagi, Y. and Berger, I. (2012) MultiBac: expanding the research toolbox for multiprotein complexes. *Trends Biochem Sci,* 37, 49-57.

32. Hohlbein, J., Aigrain, L., Craggs, T. D., Bermek, O., Potapova, O., Shoolizadeh, P., Grindley, N. D., Joyce, C. M. and Kapanidis, A. N. (2013) Conformational land-scapes of DNA polymerase I and mutator derivatives establish fidelity checkpoints for nucleotide insertion. *Nat Commun,* 4, 2131.

33. Ishmukhametov, R. R., Russell, A. N. and Berry, R. M. (2016) A modular platform for one-step assembly of multi-component membrane systems by fusion of charged proteoliposomes. *Nat Commun,* 7, 13025.

34. Berglund, A. J. (2010) Statistics of camera-based single-particle tracking. *Phys Rev E Stat Nonlin Soft Matter Phys,* 82, 011917.

35. Corporation, O. C.

36. Hutchinson, E. C., Charles, P. D., Hester, S. S., Thomas, B., Trudgian, D., Martinez-Alonso, M. and Fodor, E. (2014) Conserved and host-specific features of influenza virion architecture. *Nat Commun,* 5, 4816.

37. Duchi, D., Gryte, K., Robb, N. C., Morichaud, Z., Sheppard, C., Brodolin, K., Wigneshweraraj, S. and Kapanidis, A. N. (2018) Conformational heterogeneity and bubble dynamics in single bacterial transcription initiation complexes. *Nucleic Acids Res,* 46, 677-688.

38. Robb, N. C., Cordes, T., Hwang, L. C., Gryte, K., Duchi, D., Craggs, T. D., Santoso, Y., Weiss, S., Ebright, R. H. and Kapanidis, A. N. (2013) The transcription bubble of the RNA polymerase-promoter open complex exhibits conformational heterogeneity and millisecond-scale dynamics: implications for transcription start-site selection. *J Mol Biol,* 425, 875-885.

39. Robb, N. C., Te Velthuis, A. J., Wieneke, R., Tampe, R., Cordes, T., Fodor, E. and Kapanidis, A. N. (2016) Single-molecule FRET reveals the pre-initiation and initiation conformations of influenza virus promoter RNA. *Nucleic Acids Res,* 44, 10304-10315.

The following are aspects of the invention.

1. A method of functionalizing a particle with a negatively charged polymer; the particle having a negatively charged surface and a lipid coating; wherein the method comprises contacting said particle with (i) a polyvalent cation and (ii) said polymer; such that the polymer binds to the particle thereby functionalizing the particle.

2. A method according to aspect 1 wherein the particle is a nanoparticle.

3. A method according to aspect 1 or aspect 2 wherein the particle is an enveloped virus particle.

4. A method according to aspect 3 wherein the virus is selected from herpesviridae, poxviridae, pneumoviri-dae, hepadnaviridae, flaviviridae, togaviridae, corona-viridae, hepatitis D virus, orthomyxoviridae, paramyxoviridae, rhabdoviridae, bunyaviridae, filo-viridae, baculoviridae and retroviridae.

5. A method according to aspect 3 or aspect 4 wherein the virus is an influenza virus.

6. A method according to any one of aspects 3 to 5 wherein the virus is present in a biological fluid, wherein preferably the biological fluid is allantoic fluid or is a cell culture medium.

7. A method according to any one of the preceding aspects wherein the polyvalent cation is a divalent metal cation.

8. A method according to any one of the preceding aspects wherein the polyvalent cation is $Ca^{2+}$ 9. A method according to aspect 8 wherein the Ca$^{2+}$ is provided as CaCl$_2$.

10. A method according to any one of the preceding aspects wherein the negatively charged polymer is a polynucleotide, a polypeptide, a polysaccharide or a negatively charged polyether.

11. A method according to any one of the preceding aspects wherein the negatively charged polymer is a polynucleotide, preferably wherein the polynucleotide is an oligonucleotide.

12. A method according to any one of the preceding aspects wherein the negatively charged polymer comprises a detectable label and/or an immobilisation tag and/or one or more reactive functional groups.

13. A method according to aspect 12 wherein the detectable label is an optically detectable label, preferably a fluorescent or chemiluminescent label.

14. A method according to aspect 12 wherein the immobilisation tag is an affinity tag, preferably a biotin tag.

15. A method according to any one of the preceding aspects, wherein the particle is an enveloped virus particle; the polyvalent cation is Ca$^{2+}$ and the negatively charged polymer is a polynucleotide;
said method comprising contacting in solution at least about 10$^2$ PFU/mL viral particles with at least about 10 mM Ca$^{2+}$ and at least about 1 nM polynucleotide.

16. A method according to any one of the preceding aspects, comprising contacting the particle with the polyvalent cation and the negatively charged polymer for less than about 30 minutes, preferably for less than about 15 minutes.

17. A method according to any one of the preceding aspects, wherein the particle is an enveloped virus particle; the method further comprising the step of binding the functionalized virus particle to a host cell.

18. A method according to any one of the preceding aspects further comprising releasing the polymer from the functionalized particle by contacting the functionalized particle with a chelating agent for the polyvalent cation.

19. A method according to any one of the preceding aspects, wherein the particle is an enveloped virus particle and the virus is of a particular type, and the method further comprises identifying the enveloped virus particle as being a virus of that particular type using a method for identifying viruses of that particular type.

20. A functionalized particle which is obtainable by a method as defined in any one of aspects 1 to 16.

21. A functionalized particle, comprising:
a particle having a negatively charged surface and a lipid coating;
a negatively charged polymer; and
a polyvalent cation which binds the polymer to the particle.

22. A functionalized particle according to aspect 21 wherein:
the particle is as defined in any one of aspects 2 to 6; and/or
the polyvalent cation is as defined in any one of aspects 7 to 9; and/or
the negatively charged polymer is as defined in any one of aspects 10 to 14.

23. A composition comprising a functionalized particle as defined in aspect 21 or aspect 22 and a carrier medium.

24. A method of binding a functionalized virus particle to a host cell, which method comprises binding to a host cell a functionalized particle as defined in any one of aspects 20 to 22; wherein the particle is an enveloped virus particle.

25. A method of releasing a polymer from a functionalized particle as defined in any one of aspects 20 to 22, which method comprises contacting the functionalized particle with a chelating agent for the polyvalent cation.

26. A method of optically tracking a particle having a negatively charged surface and a lipid coating; the method comprising:
a) functionalizing the particle with a negatively charged polymer by a method as defined in any one of aspects 1 to 19, wherein the negatively charged polymer comprises an optically detectable label; and
b) optically tracking the optically detectable label thereby tracking the particle;
wherein preferably the particle is an enveloped viral particle.

27. A method of tracking a particle as defined in any one of aspects 20 to 22, wherein the negatively charged polymer comprises an optically detectable label, and the method comprises optically tracking said optically detectable label.

28. A method of functionalizing the surface of a particle having a negatively charged surface and a lipid coating; the method comprising functionalizing the particle with a negatively charged polymer in a method according to any one of aspects 1 to 19; wherein the negatively charged polymer comprises one or more reactive functional groups; such that the polymer binds to the surface of the particle thereby functionalizing the surface of the particle;
wherein preferably the particle is an enveloped viral particle.

29. A method of isolating enveloped viral particles from a sample, comprising:
a) functionalizing the enveloped viral particles in the sample with a negatively charged polymer according to any one of aspects 3 to 19; wherein the negatively charged polymer comprises an immobilization tag;
b) contacting the immobilisation tag with a substrate therefor such that the immobilisation tag binds to the substrate;
c) isolating the substrate from the sample; and
d) optionally releasing the viral particles from the substrate.

30. A method of quantifying enveloped virus particles in a sample, comprising:
a) functionalizing the enveloped viral particles in the sample with a negatively charged polymer according to any one of aspects 3 to 19; wherein the negatively charged polymer comprises a detectable label;
b) detecting the detectable label; and
c) determining the number or concentration of detectable labels in the sample thereby quantifying the number or concentration of labelled viral particles in the sample.

31. A method according to aspect 30 wherein the detectable label is a fluorescent label and wherein detecting the fluorescent label involves passing the labelled viral particles in the sample through a fluidics system having a detection zone and comprising an optical detector, photo-illuminating the detection zone and thereby detecting fluorescence of the labelled viral particles in the confocal volume.

32. A method of assessing enveloped viral aggregation in a sample, comprising:

a) functionalizing the enveloped viral particles in the sample with a negatively charged polymer according to any one of aspects 3 to 19; wherein the negatively charged polymer comprises an optically detectable label; wherein the individual viruses in the population have a known size;

b) optically tracking motion of the labelled viral particles;

c) determining an average diffusion coefficient for the labelled viral particles in the sample and thereby obtaining an estimate of the particulate size of the labelled viral particles;

d) comparing the known size of the viruses in the population with the estimated particulate size of the labelled viral particles and thereby assessing the extent of viral aggregation in the sample.

33. A method of identifying a virus of a particular type, which method comprises:

a) functionalizing enveloped viral particles in a sample with a negatively charged polymer by a method as defined in any one of aspects 3 to 19; wherein the negatively charged polymer comprises an immobilisation tag and, optionally, a first detectable label;

b) contacting the immobilisation tag with a substrate therefor such that the immobilisation tag binds to the substrate and thereby immobilises the enveloped viral particles on the substrate;

c) optionally, detecting the first detectable label;

d) contacting the enveloped viral particles with an agent for identifying viruses of a particular type, optionally wherein the agent comprises a second detectable label; and e) identifying any viruses of the particular type, optionally by detecting the second detectable label;

optionally wherein the agent comprises a strain-specific antibody, aptamer or complementary genome probe.

34. A method according to any one of aspects 23 to 33 wherein:

the enveloped viral particles comprise a virus as defined in any one of aspects 4 to 6; and/or the polyvalent cation is as defined in any one of aspects 7 to 9; and/or the negatively charged polymer is as defined in any one of aspects 10 to 14; and/or the particle is functionalized as defined in any one of aspects 15 to 16; and/or the method further comprises the steps set out in any one of aspects 17 to 19.

35. A kit comprising:

(i) a particle having a negatively charged surface and a lipid coating;

(ii) a negatively charged polymer; and (iii) a polyvalent cation for binding the polymer to the particle

The invention claimed is:

1. A method of labelling a particle having an anionic lipid bilayer with a fluorescently labelled negatively charged non-specific polynucleotide, comprising:

contacting a particle having an anionic lipid bilayer with a fluorescently labelled negatively charged non-specific polynucleotide in the presence of a polyvalent cation, thereby creating a labelled particle.

2. The method of claim 1 wherein the particle is a nanoparticle.

3. The method of 1 wherein the particle is an enveloped virus particle.

4. The method of claim 3 wherein the virus is an influenza virus and/or is selected from the group consisting of herpesviridae, poxviridae, pneumoviridae, hepadnaviridae, flaviviridae, togaviridae, coronaviridae, hepatitis D virus, orthomyxoviridae, paramyxoviridae, rhabdoviridae, bunyaviridae, filoviridae, baculoviridae and retroviridae.

5. The method of claim 3 wherein the virus is present in a biological fluid.

6. The method of claim 1 wherein the polyvalent cation is a divalent metal cation.

7. The method of claim 1 wherein the polyvalent cation is $Ca^{2+}$ and/or is provided as $CaCl_2$.

8. The method of claim 1 wherein the fluorescently labelled negatively charged non-specific polynucleotide comprises an immobilisation tag and/or one or more reactive functional groups.

9. The method of claim 8 wherein:
the immobilisation tag is an affinity tag; or
the immobilisation tag is a biotin tag.

10. The method of claim 1, wherein the particle is an enveloped virus particle and the polyvalent cation is $Ca^{2+}$;
said method comprising contacting in solution at least about $10^2$ PFU/mL viral particles with at least about 10 mM $Ca^{2+}$ and at least about 1 nM polynucleotide.

11. The method of claim 1, comprising contacting the particle with the polyvalent cation and the fluorescently labelled negatively charged non-specific polynucleotide for less than about 30 minutes.

12. The method of claim 1, wherein the particle is an enveloped virus particle; the method further comprising the step of binding the functionalized virus particle to a host cell.

13. The method of claim 1 further comprising releasing the fluorescently labelled negatively charged non-specific polynucleotide from the functionalized particle by contacting the functionalized particle with a chelating agent for the polyvalent cation.

14. The method of claim 1 wherein the particle comprises a naturally occurring particle.

15. The method of claim 14 wherein the naturally occurring particle comprises a cell.

16. The method of claim 15 wherein the cell is at least one of a plant cell, a fungal cell, a yeast cell, an animal cell, an insect cell, or a bacterial cell.

17. The method of claim 5 wherein the biological fluid comprises at least one of blood, plasma, serum, urine, lymph, saliva, mucus, amniotic, or allantoic fluid.

* * * * *